United States Patent
Miyake et al.

(10) Patent No.: US 10,590,018 B2
(45) Date of Patent: Mar. 17, 2020

(54) METHOD FOR FORMING AEROBIC GRANULES, DEVICE FOR FORMING AEROBIC GRANULES, METHOD FOR TREATING WASTEWATER, AND DEVICE FOR TREATING WASTEWATER

(71) Applicant: ORGANO CORPORATION, Tokyo (JP)

(72) Inventors: Masaki Miyake, Tokyo (JP); Yoshiaki Hasebe, Tokyo (JP); Masahiro Eguchi, Tokyo (JP)

(73) Assignee: ORGANO CORPORATION, Tokyo (JP)

( * ) Notice: Subject to any disclaimer, the term of this patent is extended or adjusted under 35 U.S.C. 154(b) by 161 days.

(21) Appl. No.: 15/559,635

(22) PCT Filed: Mar. 30, 2016

(86) PCT No.: PCT/JP2016/060408
§ 371 (c)(1),
(2) Date: Sep. 19, 2017

(87) PCT Pub. No.: WO2016/159091
PCT Pub. Date: Oct. 6, 2016

(65) Prior Publication Data
US 2018/0339925 A1    Nov. 29, 2018

(30) Foreign Application Priority Data

Mar. 31, 2015 (JP) .................................. 2015-073511
May 27, 2015 (JP) .................................. 2015-107925

(51) Int. Cl.
*C02F 3/02* (2006.01)
*C02F 3/12* (2006.01)
(Continued)

(52) U.S. Cl.
CPC ................ *C02F 3/02* (2013.01); *C02F 3/006* (2013.01); *C02F 3/1263* (2013.01); *C12N 1/20* (2013.01);
(Continued)

(58) Field of Classification Search
CPC .......... C02F 3/02; C02F 3/1263; C02F 3/006; C02F 2209/10; C02F 2209/08; C02F 3/30; C02F 2003/001; C12N 1/20; Y02W 10/15
(Continued)

(56) References Cited

U.S. PATENT DOCUMENTS

2003/0159991 A1    8/2003   Tay et al.
2007/0158265 A1*   7/2007   Cote ........................ C02F 3/223
                                                              210/605
(Continued)

FOREIGN PATENT DOCUMENTS

CN    1596224 A    3/2005
EP    3279154      2/2018
(Continued)

OTHER PUBLICATIONS

Machine-generated English Translaton of JP 2007-136367, generated on Jun. 28, 2019.*
(Continued)

*Primary Examiner* — Fred Prince
(74) *Attorney, Agent, or Firm* — Greenblum & Bernstein, P.L.C.

(57) ABSTRACT

Provided is a method for forming aerobic granules in which a semibatch reactor for forming granules is used, the method involving repeatedly carrying out an inflowing step for causing organic-matter-containing wastewater that includes organic matter to flow in, a biological treatment step for biologically treating substances to be treated in the organic-
(Continued)

matter-containing drainage water by using microbial sludge, a settling step for allowing the microbial sludge to settle out, and a discharge step for discharging biologically treated water which has been biologically treated, wherein the reaction time is adjusted such that the value obtained by dividing the total cycle time by the reaction time and multiplying the resulting quotient by the ratio of the MLSS concentration to the BOD load charged into the semibatch reactor is within a range of 0.05 to 0.25 kgBOD/kgMLSS/d, and the sludge is drawn such that the sludge retention period is 5 to 25 days.

11 Claims, 19 Drawing Sheets

(51) Int. Cl.
  *C02F 3/00* (2006.01)
  *C12N 1/20* (2006.01)
  *C02F 3/30* (2006.01)
(52) U.S. Cl.
  CPC .......... *C02F 3/30* (2013.01); *C02F 2003/001* (2013.01); *C02F 2209/08* (2013.01); *C02F 2209/10* (2013.01); *Y02W 10/15* (2015.05)
(58) Field of Classification Search
  USPC ....... 210/601, 615, 616, 617, 620, 621, 622, 210/623, 150, 151, 259
  See application file for complete search history.

(56) References Cited

U.S. PATENT DOCUMENTS

| | | | | |
|---|---|---|---|---|
| 2009/0127190 | A1* | 5/2009 | Ong | C02F 3/1263 210/617 |
| 2013/0075327 | A1* | 3/2013 | Yuan | C02F 3/1205 210/605 |

FOREIGN PATENT DOCUMENTS

| | | |
|---|---|---|
| JP | 2005-517532 | 6/2005 |
| JP | 2006-88158 | 4/2006 |
| JP | 2006-346572 | 12/2006 |
| JP | 2007-136367 | 6/2007 |
| JP | 2008-212878 | 9/2008 |
| JP | 2008-284427 | 11/2008 |
| JP | 4804888 | 11/2011 |
| JP | 4975541 | 7/2012 |
| JP | 2014-136188 | 7/2014 |
| WO | 2004/024638 | 3/2004 |
| WO | 2012/077381 | 6/2012 |

OTHER PUBLICATIONS

International Search Report issued in Patent Application No. PCT/JP2016/060408, dated Jun. 21, 2016.
International Preliminary Report on Patentability issued in PCT/JP2016/060408, dated Oct. 12, 2017.
Official Action dated Jan. 29, 2019 in European application No. 16 772 972.2 (in English).
Notice of Grounds for Rejection dated Mar. 19, 2019 in Japanese patent application No. 2015-073511, and English language translation thereof.
Third Party Observations with English Translation as filed in European Application No. 1677297.2 on Feb. 21, 2018.
"Wastewater Treatment Manuals: Primary, Secondary, and Tertiary Treatment", Environmental Protection Agency, Ireland, 1997.
"Merkblatt DWA-M 210", Belebungsanlagen mit Aufstaubetrieb (SBR), Deutsche Vereinigung fur Wasserwirtschaft, Abwasser und Abfall e.V., Jul. 2009.
F. Coelho et al. "Aerobic granular biomass technology; scale-up and field experience for cost-effective treatment of urban and industrial wastewater"; Proceeding IWA Biofilm Reactors Conference, 2013.
L.M.M. de Bruin et al., Biological wastewater treatment using aerobic granules—Nereda™, IWA 2006.
Extended European Search Report in respect to European Application No. 16772972.2, dated Mar. 23, 2018.
A. C. van Haandel, J. G. M. van der Lubbe, Handbook of Biological Wastewater Treatment.
L. M. M. de Bruin, M. K. de Kreuk, A. Geisen, J. Verkuijlen, M. W. Kraan, Biological Wastewater Treatment Using Aerobic Granules, (2006).
Wastewater Treatment Manuals: Primary, Secondary and Tertiary Treatment.
Merkblatt DWA-M 210, Belebungsanlagen mit Aufstaubetrieb (SBR).
F. Coelho, A. Giesen, R. Kraan, Aerobic Granular Biomass Technology.
Supplementary European Search Report for Eurpoean Application No. EP16772972 dated Mar. 15, 2018.
European Search Opinion for European Application No. EP16772972.2 dated Jul. 9, 2018.
Notice of Grounds for Rejection issued in JP patent application No. 2015-107925, dated Apr. 23, 2019, and English language translation thereof.
Office Action in TW Application No. 105109604 and English language translation thereof.
JP Information Submission Statement (Submitted Aug. 30, 2019) and English language translation thereof.
"People's Republic of China, Support Work for Grade-up Modification of Sewage Treatment Site and Operation Improvement Projects, Final Report, report-end product reference 2 • 2, small-size and mid-size sewage treatment sites, SBR, law, application evaluation and design/operation management guidelines" National City Feed and Drain Water Process Technique Research Center et al., p. 14, lines 39-42 (excerpt) (published Mar. 2013).
"Effects of Sludge Retention Times on Nutrient Removal and Nitrous Oxide Emission in Biological Nutrient Removal Processes", Int J Environ Res Public Health., Mar. 27, 2014: 11(4):3553-69 (published Mar. 2014).
Water Treatment Engineering-Theory and Application, Tetsuo IDE, Gihodo Shuppan Co., Ltd., p. 237 (published Jun. 2001).

\* cited by examiner

METHOD FOR FORMING AEROBIC GRANULES, DEVICE FOR FORMING AEROBIC GRANULES, METHOD FOR TREATING WASTEWATER, AND DEVICE FOR TREATING WASTEWATER

TECHNICAL FIELD

The present invention relates to a method for forming aerobic granules and a device for forming aerobic granules which are used for stably forming aerobic granules for aerobically biologically treating organic matter-containing wastewater containing organic matter or the like, and also relates to a method for treating wastewater and a device for treating wastewater that use the formed granules.

BACKGROUND

Conventionally, biological wastewater treatments of organic matter-containing wastewater containing organic matter or the like have used the activated sludge method that utilizes an aggregate of microbes (aerobic biological sludge) known as a flock. However, in the activated sludge method, when separating the flock (aerobic biological sludge) and the treated water in the settling tank, because the settling rate of the flock is slow, the surface area of the settling tank must sometimes be increased substantially. Further, the treatment rate of the activated sludge method depends on the sludge concentration in the biological treatment tank, and therefore the treatment rate can be increased by increasing the sludge concentration, but if the sludge concentration is increased to a value within a range from 1,500 to 5,000 mg/L, or an even higher value, then solid-liquid separation becomes difficult due to bulking or the like within the settling tank, meaning treatment cannot be maintained in some cases.

On the other hand, anaerobic biological treatments generally utilize aggregates (anaerobic biological sludge) in particulate form known as granules, which contain densely packed microbes. Granules exhibit extremely fast settling rates, and because the microbes are densely packed, the sludge concentration in the biological treatment tank can be increased, and a high-speed treatment of the wastewater can be achieved. However, anaerobic treatments sometimes suffer problems, including restrictions on the types of wastewaters that can be treated compared with aerobic treatments (the activated sludge method), and the requirement to hold the temperature of the treatment water at about 30 to 35° C. Further, if only an anaerobic treatment is used, then the water quality of the treated water tends to be poor, and in those cases where the treatment water is to be discharged into a river or the like, a separate aerobic treatment such as a biological sludge treatment is sometimes required.

In recent years, it has become clear that by performing treatment using a semibatch treatment device in which the wastewater is introduced intermittently into the reaction tank, and shortening the biological sludge settling time, granulated biological sludges having good settling properties can be formed not only with anaerobic sludges, but also with aerobic sludges (for example, see Patent Documents 1 to 4). By granulating an aerobic sludge, the average particle size can be increased to 0.2 mm or greater, and the settling rate can be increased to 5 m/h or greater. In a semibatch treatment device, treatment is performed in a single biological treatment tank via four steps, namely (1) wastewater introduction, (2) biological treatment of the treatment target substances, (3) settling of the biological sludge, and (4) discharge of the treated water. By forming the type of granulated aerobic biological sludge with good settling properties described above, the sludge concentration in the tank can be maintained at a high concentration, enabling a high-speed treatment to be achieved.

One method that has been proposed for accelerating the granulation is a method in which the settling time for the aerobic granules is shortened, thereby proactively discharging sludge having a slow settling rate from the system, but in this method, because the amount of discharged microbes fluctuates depending on changes in the sludge settling properties, forming the aerobic granules in a stable manner is sometimes difficult. Further, in the case of wastewaters such as sewage having a low BOD concentration of about 80 to 200 mg/L, another problem arises in that the aerobic granules tend to be difficult to form, even when using a semibatch reactor.

CITATION LIST

Patent Literature

Patent Document 1: WO 2004/024638
Patent Document 2: JP 2008-212878 A
Patent Document 3: JP 4975541 B
Patent Document 4: JP 4804888 B

SUMMARY

Technical Problem

Objects of the present invention are to provide a method for forming aerobic granules and a device for forming aerobic granules which can stably form aerobic granules using a semibatch reactor, and also provide a method for treating wastewater and a device for treating wastewater that use the formed granules.

Solution to Problem

The present invention provides a method for forming aerobic granules using a semibatch reactor, the method involving forming granules by repeatedly performing an introduction step of introducing an organic matter-containing wastewater containing organic matter, a biological treatment step of biologically treating treatment target substances in the organic matter-containing wastewater using a microbial sludge, a settling step of allowing the microbial sludge to settle, and a discharge step of discharging a biologically treated water that has been biologically treated, wherein the reaction time is adjusted so that the value obtained by multiplying the ratio of the MLSS concentration relative to the BOD load introduced into the semibatch reactor by [total cycle time/reaction time] falls within a range from 0.05 to 0.25 kgBOD/kgMLSS/d, and the sludge is withdrawn such that the sludge retention time is 5 to 25 days.

In the method for forming aerobic granules described above, it is preferable that the biologically treated water outlet of the semibatch reactor is provided above the wastewater inlet, and that the biologically treated water is discharged from the biologically treated water outlet by introducing the organic matter-containing wastewater into the semibatch reactor.

The present invention also provides a device for forming aerobic granules that includes a semibatch reactor that forms granules by repeatedly performing an introduction step of introducing an organic matter-containing wastewater containing organic matter, a biological treatment step of biologically treating treatment target substances in the organic matter-containing wastewater using a microbial sludge, a settling step of allowing the microbial sludge to settle, and a discharge step of discharging a biologically treated water that has been biologically treated, wherein the reaction time is adjusted so that the value obtained by multiplying the ratio of the MLSS concentration relative to the BOD load introduced into the semibatch reactor by [total cycle time/reaction time] falls within a range from 0.05 to 0.25 kgBOD/kgMLSS/d, and the sludge is withdrawn such that a sludge retention time is 5 to 25 days.

In the device for forming aerobic granules described above, it is preferable that the device has the biologically treated water outlet for the semibatch reactor provided above the wastewater inlet, and that the biologically treated water is discharged from the biologically treated water outlet by introducing the organic matter-containing wastewater into the semibatch reactor.

The present invention also provides a method for treating a wastewater, the method involving supplying granules formed by the method for forming aerobic granules described above to a continuous biological treatment tank used for biologically treating an organic matter-containing wastewater with a biological sludge, while the organic matter-containing wastewater is introduced continuously.

In the method for treating a wastewater described above, it is preferable that the granules are a granular sludge having a particle size of 200 µm or greater, and that the BOD sludge load of the continuous biological treatment tank is within a range from 0.08 to 0.2 kgBOD/kgMLVSS/d.

In the method for treating a wastewater described above, the continuous biological treatment tank preferably includes multiple reaction tanks.

The method for treating a wastewater described above preferably includes a sludge return step of separating the biological sludge by a solid-liquid separation from the biological treatment liquid that has undergone treatment in the continuous biological treatment tank, and then returning the separated biological sludge to the continuous biological treatment tank, and the hydraulic retention time for the continuous biological treatment tank, determined from the sum of the flow rate of wastewater introduced into the continuous biological treatment tank and the flow rate of the aforementioned biological sludge returned to the continuous biological treatment tank, and the volume of the continuous biological treatment tank, is preferably within a range from 5 hours to 10 hours.

In the method for treating a wastewater described above, it is preferable that in the introduction step of the aforementioned method for forming aerobic granules, a portion of the wastewater supplied to the continuous biological treatment tank is introduced into the semibatch reactor.

The present invention also provides a device for treating a wastewater that includes a continuous biological treatment tank used for biologically treating an organic matter-containing wastewater with a biological sludge, while the organic matter-containing wastewater is introduced continuously, wherein granules formed by the method for forming aerobic granules described above are supplied to the continuous biological treatment tank.

In the device for treating a wastewater, it is preferable that the granules are a granular sludge having a particle size of 200 µm or greater, and that the BOD sludge load of the continuous biological treatment tank is within a range from 0.08 to 0.2 kgBOD/kgMLVSS/d.

Advantageous Effects of Invention

The present invention is able to provide a method for forming aerobic granules and a device for forming aerobic granules which can stably form aerobic granules using a semibatch reactor, and is also able to provide a method for treating wastewater and a device for treating wastewater that use the formed granules.

DESCRIPTION OF EMBODIMENTS

Embodiments of the present invention are described below. These embodiments are merely examples of implementing the present invention, and the present invention is in no way limited by these embodiments.

<Method for Forming and Device for Forming Aerobic Granules>

Figure 1:
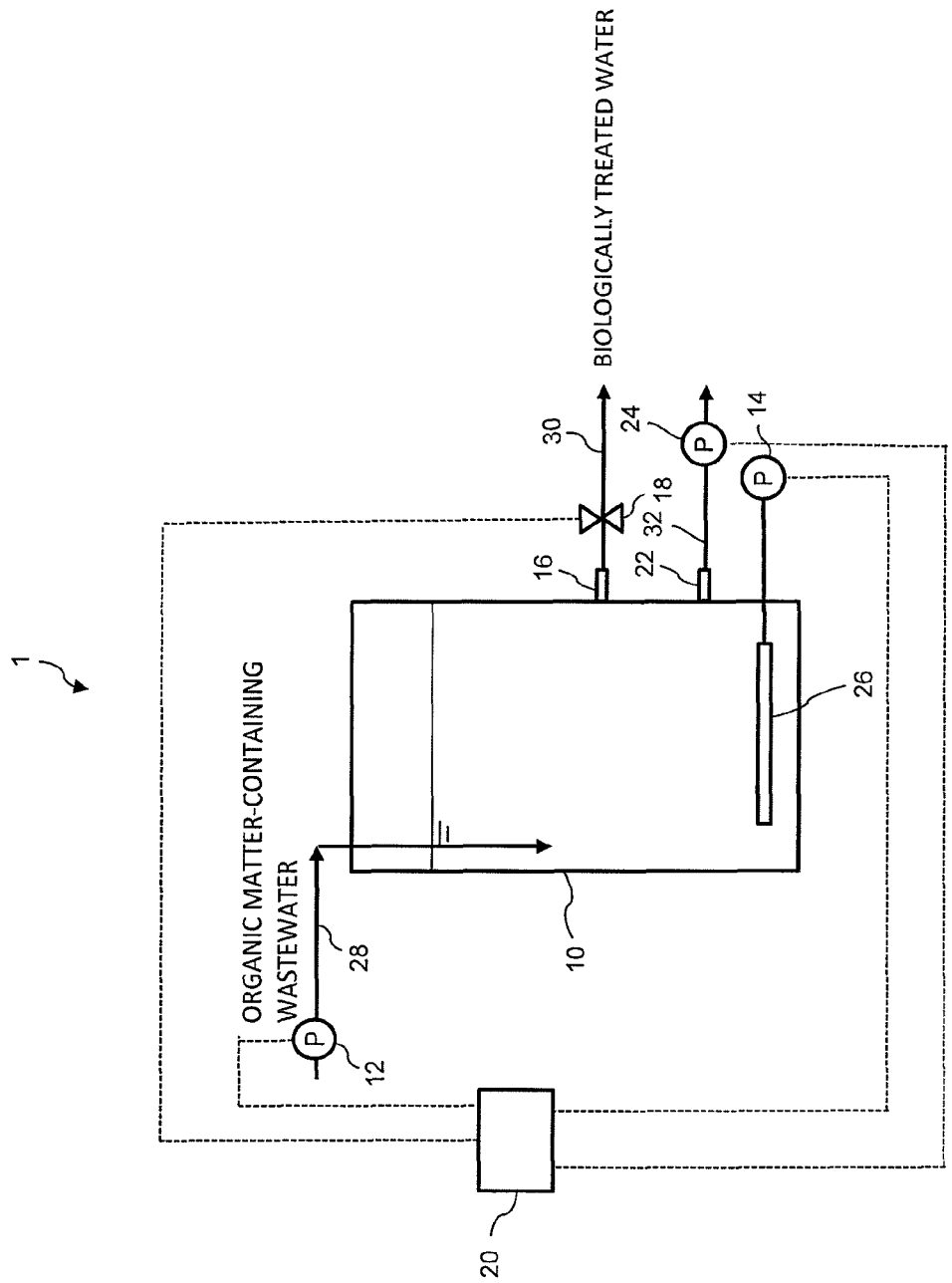
FIG. 1 is a schematic diagram illustrating one example of a device for forming aerobic granules according to an embodiment of the present invention.

The outline of one example of a device for forming aerobic granules according to an embodiment of the present invention is shown in FIG. 1, and the structure of that device is described below. The granule formation device 1 is provided with a semibatch reactor 10. In the granule formation device 1, a wastewater supply line 28 is connected to a wastewater inlet of the semibatch reactor 10 via a wastewater inlet pump 12. A biologically treated water line 30 is connected to a biologically treated water outlet 16 of the semibatch reactor 10 via a biologically treated water discharge valve 18, and a sludge withdrawal line 32 is connected to a sludge withdrawal port 22 via a sludge withdrawal pump 24. An aerator 26 connected to an aeration pump 14 is installed in the lower portion inside the semibatch reactor 10. The wastewater inlet pump 12, the biologically treated water discharge valve 18, the sludge withdrawal pump 24 and the aeration pump 14 may each be connected by electrical connection or the like to a control device 20.

The granule formation device 1 is operated, for example, using the type of cycle described below.

(1) Introduction step: the wastewater inlet pump 12 is activated, and a prescribed amount of an organic matter-containing wastewater is introduced into the semibatch reactor 10 through the wastewater supply line 28.

Figure 3:
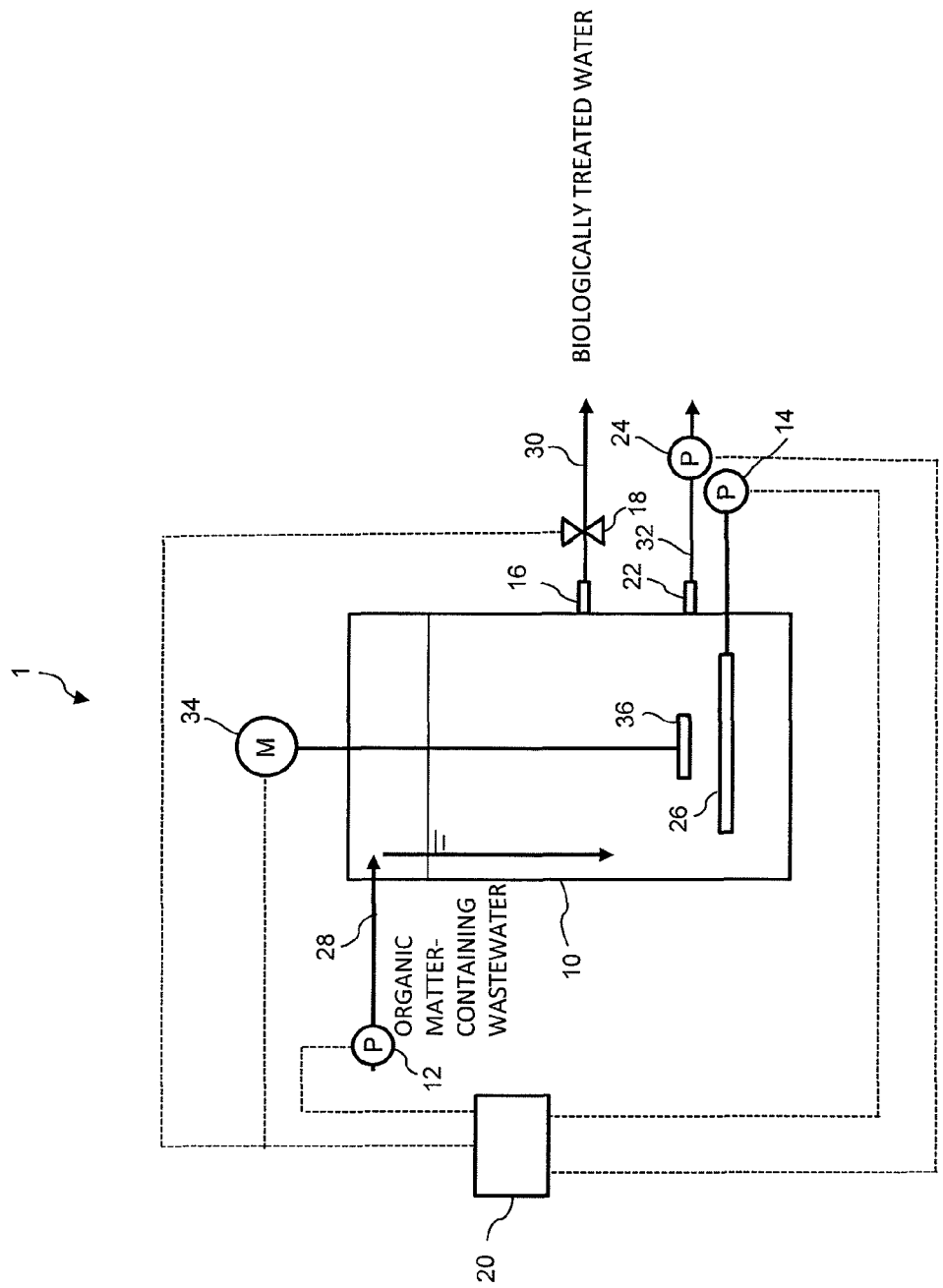
FIG. 3 is a schematic diagram illustrating another example of a device for forming aerobic granules according to an embodiment of the present invention.

(2) Biological treatment step: the wastewater inlet pump 12 is stopped, an oxygen-containing gas such as air is supplied to the semibatch reactor 10 from the aeration pump 14, and the treatment target substances in the organic matter-containing wastewater inside the semibatch reactor 10 are treated biologically with a microbial sludge. The biological reactions are not limited to aerobic reactions, and anoxic reactions can also be performed by stirring the wastewater without supplying air or the like, or a combination of aerobic reactions and anoxic reactions may occur. An anoxic state describes a state in which although no dissolved oxygen exists, oxygen and the like derived from nitrites or nitrates does exist. For example, as illustrated in FIG. 3, a stirring device formed from a motor 34, a stirring blade 36 and a shaft or the like that connects the motor 34 and the stirring blade 36 may be installed in the semibatch reactor 10, and stirring may then be performed using the stirring device, with the aeration pump 14 stopped. The stirring device is not limited to the configuration described above.

(3) Settling step: the aeration pump 14 is stopped, and the device is left to stand for a prescribed period of time to allow the sludge inside the semibatch reactor 10 to settle.

(4) Discharge step: by opening the biologically treated water discharge valve 18, the supernatant water obtained in the settling step is discharged from the biologically treated water outlet 16 through the biologically treated water line 30 as a biologically treated water. At this time, the biologically treated water may also be discharged using a pump instead of using the biologically treated water discharge valve.

By repeating the cycle of the above steps (1) to (4), granules composed of granular aggregates of tightly packed microbes are formed. Activation and stopping of the wastewater inlet pump 12, the sludge withdrawal pump 24, the aeration pump 14 and the stirring device motor 34, and opening and closing of the biologically treated water discharge valve 18 may be controlled by the control device 20.

The granular sludge formed in the semibatch reactor 10 is a sludge formed as a result of self-granulation, and is, for example, a biological sludge having an average particle size of 0.2 mm or greater, or an SVI5 value, which is an indicator of the settling properties, of not more than 80 mL/g. Further, in the present embodiment, whether or not a granular sludge has been formed can be ascertained, for example, by measuring the SVI that acts as an indicator of the sludge settling properties. Specifically, the SVI value is measured regularly by subjecting the sludge inside the semibatch reactor 10 to a settling properties test, and when the SVI5 value calculated from the volume proportions obtained after settling for 5 minutes reaches a specified value or lower (for example, not more than 80 mL/g), a granular sludge can be deemed to have formed. Alternatively, the particle size distribution of the sludge inside the semibatch reactor 10 is measured, and when the average particle size reaches a specified value or higher (for example, 0.2 mm or greater), a granular sludge can be deemed to have formed (and the smaller the SVI value and the larger the average particle size, the more favorable the granular sludge).

The inventors of the present invention discovered that by adjusting the reaction time so that the value obtained by multiplying the ratio of the MLSS concentration relative to the BOD load introduced into the semibatch reactor (namely, BOD/MLSS) by [total cycle time/reaction time] falls within a range from 0.05 to 0.25 kgBOD/kgMLSS/d, and withdrawing the sludge such that the sludge retention time in the semibatch reactor 10 is 5 to 25 days, aerobic granules could be formed in a stable manner.

Figure 2:
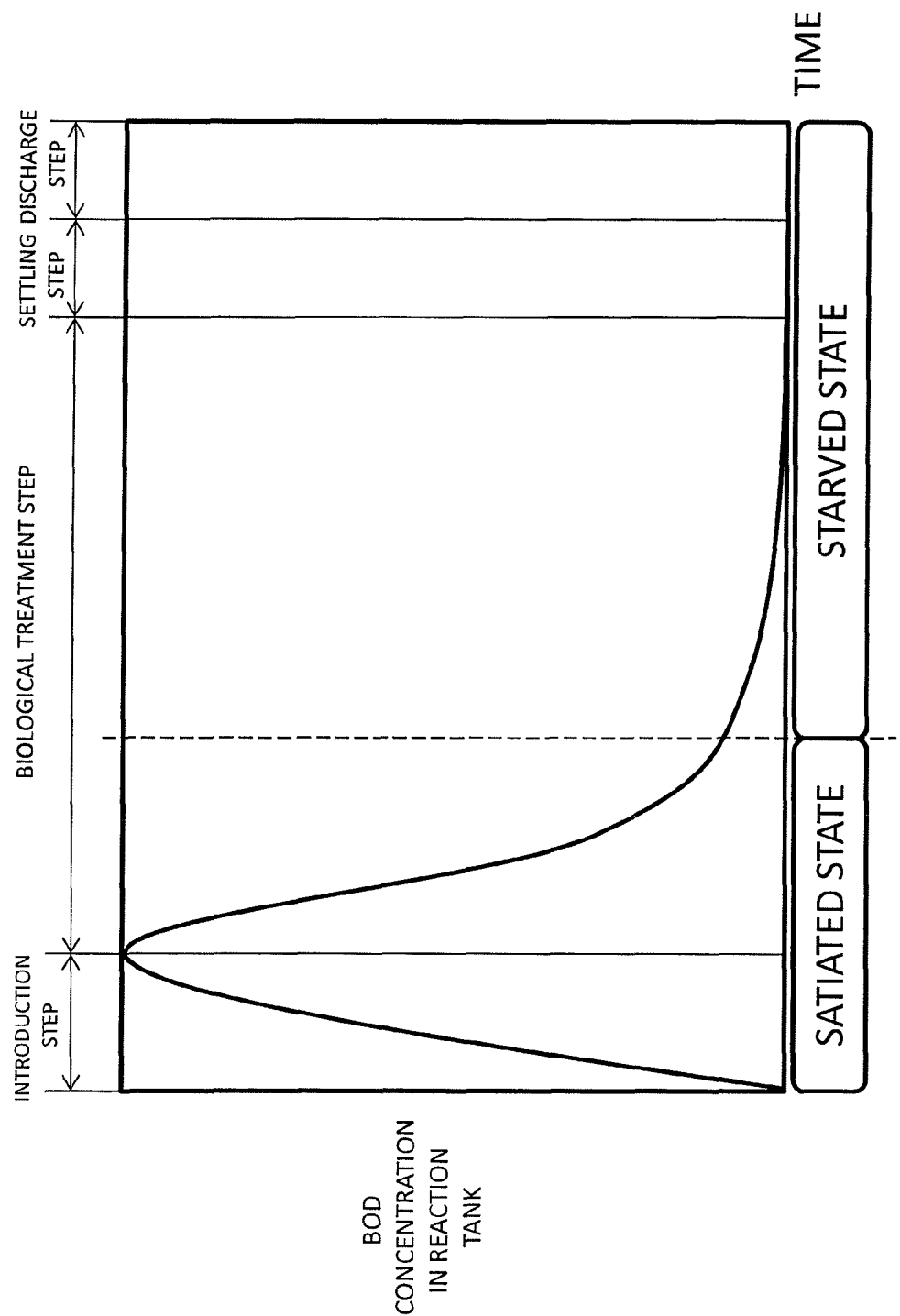
FIG. 2 is a diagram illustrating the relationship between the BOD concentration and the treatment time for one batch in a semibatch reactor.

The inventors of the present invention discovered that determining the time for the above biological treatment step (2) had a large effect on the granulation. The inventors of the present invention postulated the granule formation mechanism described below. FIG. 2 illustrates the relationship between the BOD concentration and the treatment time for one batch in a semibatch reactor. As illustrated in FIG. 2, when the organic matter-containing wastewater introduction step is finished and the process shifts to the biological treatment step, the BOD concentration inside the semibatch reactor decreases with the treatment time as a result of the degradation action of the microbes. During this period, because the BOD in the semibatch reactor is higher than the amount of microbes, a state in which residual organic matter exists within the semibatch reactor is obtained (a satiated state). As degradation of the organic matter by the microbes proceeds, and the BOD concentration inside the semibatch reactor falls, the treatment rate decreases, and eventually falls to substantially zero. In other words, because the residual BOD is small compared with the amount of microbes in the semibatch reactor, a starved state for the microbes is generated. Subsequently, the process shifts to the settling step and the biologically treated water discharge step. By repeating this cycle, granulation of the biological sludge proceeds inside the semibatch reactor. In this mechanism for forming granules in the semibatch reactor, formation of the type of organic matter concentration gradient described above inside the semibatch reactor during the cycle is important. Further, as a result of repeating the starved state and the satiated state, the bacteria produce viscous substances, and these viscous substances causes the bacteria and the like to adhere strongly together, leading to the formation of granules.

In one cycle, if the amount of microbes (MLSS concentration) inside the semibatch reactor is high relative to the BOD load introduced into the semibatch reactor, then the organic matter degradation rate in the satiated state increases, and the length of the satiated time shortens. In contrast, if the amount of microbes (MLSS concentration) inside the semibatch reactor is low, then the organic matter degradation rate in the satiated state slows, and the length of the satiated time lengthens. In other words, if the reaction time is assumed to be the same, then depending on the amount of microbes relative to the BOD load introduced into the semibatch reactor, the ratio between the length of the satiated time and the length of the starved time following the satiated time varies. By controlling this ratio of satiated time/starved time, granules can be formed in a stable manner. This ratio between the satiated time and the starved time can be represented by the ratio of the amount of microbes relative to the BOD load (BOD/MLSS). Further, because the steps other than the biological treatment step do not contribute significantly to the biological reaction, by performing the evaluation on the basis of the value (hereafter sometimes referred to as the "A value") obtained by multiplying the ratio of the MLSS concentration to the BOD load by [total cycle time/reaction time], the ratio of satiated time/starved time can be controlled more accurately. Here, the "total cycle time" indicates the total time for the introduction step (1), the biological treatment step (2), the settling step (3) and the discharge step (4) (or in the case of the configurations illustrated in FIG. 4 and FIG. 5 described below, the total time of an introduction step/discharge step (1), the biological treatment step (2) and the settling step (3)), and the "reaction time" indicates the time of the biological treatment step (2).

The A value that determines this ratio of satiated time/starved time is preferably within a range from 0.05 to 0.25 kgBOD/kgMLSS/d, and more preferably within a range from 0.1 to 0.16 kgBOD/kgMLSS/d. If this value is less than 0.05 kgBOD/kgMLSS/d, then the length of the starved time becomes too long, which may lead to disintegration of the granules. Further, if this value is greater than 0.25 kgBOD/kgMLSS/d, then the satiated time becomes too long, and the viscous substances are less likely to be produced, meaning the granules are less likely to form.

However, sometimes forming the granules in a stable manner simply by controlling this ratio of satiated time/starved time can be difficult. By combining this satiated time/starved time ratio with control of the amount of sludge withdrawn, the granules can be produced in a stable manner.

The sludge retention time is also recorded as SRT, and is one indicator of the sludge management. Specifically, the SRT is represented by the following formula.

SRT [d]=amount of sludge [kg] that exists in the system/amount of sludge discharged from the system in a single day [kg/d]

An SRT value within a range from 5 to 25 days is preferable for stable formation of the granules, and a value within a range from 10 to 15 days is more preferred. The sludge withdrawal pump 24 illustrated in FIG. 1 and FIG. 3 may be activated, and the sludge withdrawn from the sludge withdrawal port 22 through the sludge withdrawal line 32, so as to achieve an SRT value within a range from 5 to 25 days.

If the SRT is longer than 25 days, then although large amounts of microbes having a comparatively slow growth rate are retained, microbes having a comparatively fast growth rate tend to die out. Further, if the SRT is shortened to less than 5 days, then it is thought that a state is obtained in which microbes having a comparatively fast growth rate predominate, with the abundance of microbes having a comparatively slow growth rate being much lower. The effect of the SRT on the granulation is not entirely clear, but it is thought that the respective abundance levels of these microbes having a comparatively fast growth rate and microbes having a comparatively slow growth rate are important.

Furthermore, it is thought that the SRT also affects the abundance of protozoa and metazoa, which are particular types of microbes. The longer the SRT becomes, the more higher-level protozoa→metazoa appear instead of bacteria. These protozoa and metazoa prey on bacteria. There are a large variety of these protozoa and metazoa, including those that prey on the bacteria that form the flock sludge and those that prey on dispersed-state bacteria, and therefore it is thought that in order to stably form granules composed mainly of bacteria, setting the SRT to a long time is disadvantageous. Setting the SRT to a short time is also thought to be disadvantageous, because the granule formation time is too short.

When the "A value" falls below 0.05, namely when the ratio of the amount of microbes relative to the introduced BOD amount is large, the proportion of microbes that can be grown is small, and therefore the amount of sludge withdrawn cannot be increased, meaning reducing the SRT to shorter than 30 days may be difficult, and about 25 days is the limit.

The organic matter-containing wastewater that represents the treatment target for the method for forming granules according to the present embodiment is an organic wastewater containing biodegradable organic matter, such as a food processing plant wastewater, a chemical plant wastewater, a semiconductor plant wastewater, a machinery plant wastewater, sewage or human waste. Further, when the wastewater contains hardly biodegradable organic matter, the wastewater can be converted to a treatable target substance by performing a physiochemical treatment such as an ozone treatment or a Fenton treatment in advance, to convert the hardly biodegradable organic matter to biodegradable components. Furthermore, the method for forming granules according to the present embodiment can be used against all manner of BOD components, but oils and fats may have an adverse effect by adhering to the sludge and the granules, and therefore it is preferable that prior to introduction into the semibatch reactor, a known technique such as flotation separation, flocculation pressure flotation or adsorption is performed in advance to remove the oils and fats down to a level of about 150 mg/L or less.

The pH in the semibatch reactor 10 is preferably set within a range appropriate for typical microbes, and for example, is preferably within a range from 6 to 9, and more preferably within a range from 6.5 to 7.5. If the pH is outside this range, then an acid or alkali or the like is preferably added to adjust the pH.

The dissolved oxygen (DO) inside the semibatch reactor 10, under aerobic conditions, is typically at least 0.5 mg/L, and a concentration of 1 mg/L or higher is particularly desirable.

In terms of promoting the granulation of the biological sludge, ions that form hydroxides, such as $Fe^{2+}$, $Fe^{3+}$, $Ca^{2+}$ and $Mg^+$, are preferably added to the organic matter-containing wastewater inside the semibatch reactor 10, or to the organic matter-containing wastewater prior to introduction into the semibatch reactor 10. Most typical organic matter-containing wastewaters contain microparticles that can act as nuclei for granules, but by adding the above ions, granule nuclei formation can be accelerated.

Figure 4:
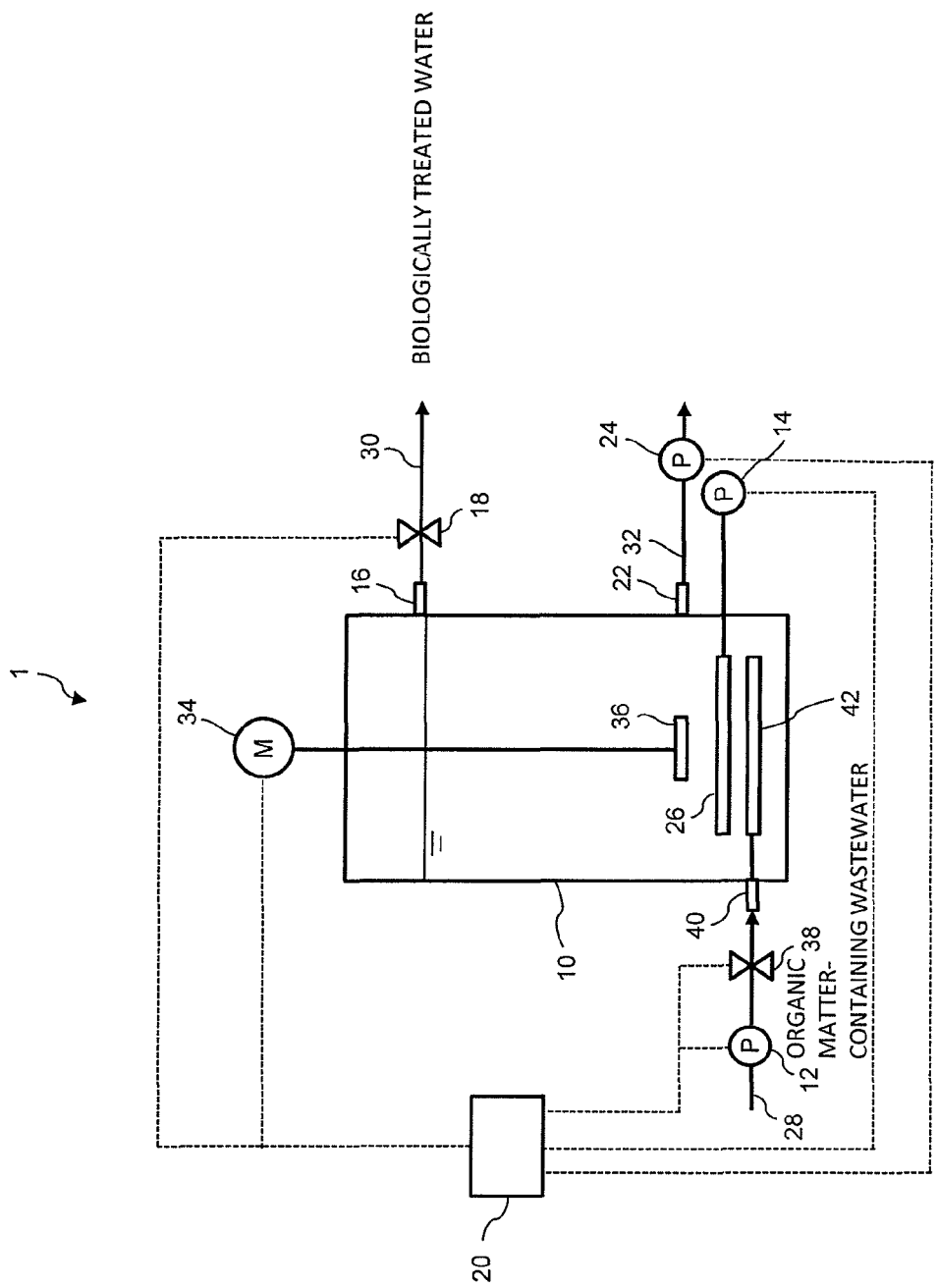
FIG. 4 is a schematic diagram illustrating another example of a device for forming aerobic granules according to an embodiment of the present invention.

Another example of the device for forming aerobic granules according to the present embodiment is shown in FIG. 4. In the granule formation device 1 illustrated in FIG. 4, the wastewater supply line 28 is connected to a wastewater inlet 40 in the lower portion of the semibatch reactor 10 via the wastewater inlet pump 12 and a wastewater inlet valve 38. A wastewater discharge unit 42 is connected to the wastewater inlet 40, and is installed in the lower portion inside the semibatch reactor 10. The biologically treated water outlet 16 of the semibatch reactor 10 is provided above the wastewater inlet 40, and the biologically treated water line 30 is connected to the biologically treated water outlet 16 via the biologically treated water discharge valve 18. The biologically treated water outlet 16 is provided above the wastewater inlet 40, and in order to prevent short-cutting of the introduced organic matter-containing wastewater and enable more efficient formation of the granules, is preferably installed as distant as possible from the wastewater inlet 40, and is more preferably installed near the water level in the settling step. The wastewater inlet pump 12, the wastewater inlet valve 38, the biologically treated water discharge valve 18, the sludge withdrawal pump 24, the aeration pump 14 and the stirring device motor 34 may each be connected by electrical connection or the like to a control device 20. The remaining configuration is the same as that of the granule formation device 1 of FIG. 3.

In the granule formation device 1 of FIG. 4, in the discharge step (4), by opening the wastewater inlet valve 38 and activating the wastewater inlet pump 12, the organic matter-containing wastewater is supplied from the wastewater inlet 40, through the wastewater supply line 28, and introduced into the semibatch reactor 10 from the wastewater discharge unit 42, thereby discharging the biologically treated water from the biologically treated water outlet 16 and through the biologically treated water line 30. Activation and stopping of the wastewater inlet pump 12, the sludge withdrawal pump 24, the aeration pump 14 and the stirring device motor 34, and opening and closing of the wastewater inlet valve 38 and the biologically treated water discharge valve 18 may be controlled by the control device 20.

In this manner, in the granule formation device 1 of FIG. 4, granules are formed by repeating a cycle composed of three steps, namely an introduction step/discharge step (1), a biological treatment step (2) and a settling step (3).

In the granule formation device 1 of FIG. 4, by discharging the biologically treated water from the biologically treated water outlet 16 by introducing the organic matter-containing wastewater into the semibatch reactor 10, granules having a comparatively small particle size are discharged with the biologically treated water, whereas those granules having a comparatively large particle size are subjected repeatedly to the cycle of steps (1) to (3), enabling more efficient granule formation.

Figure 5:
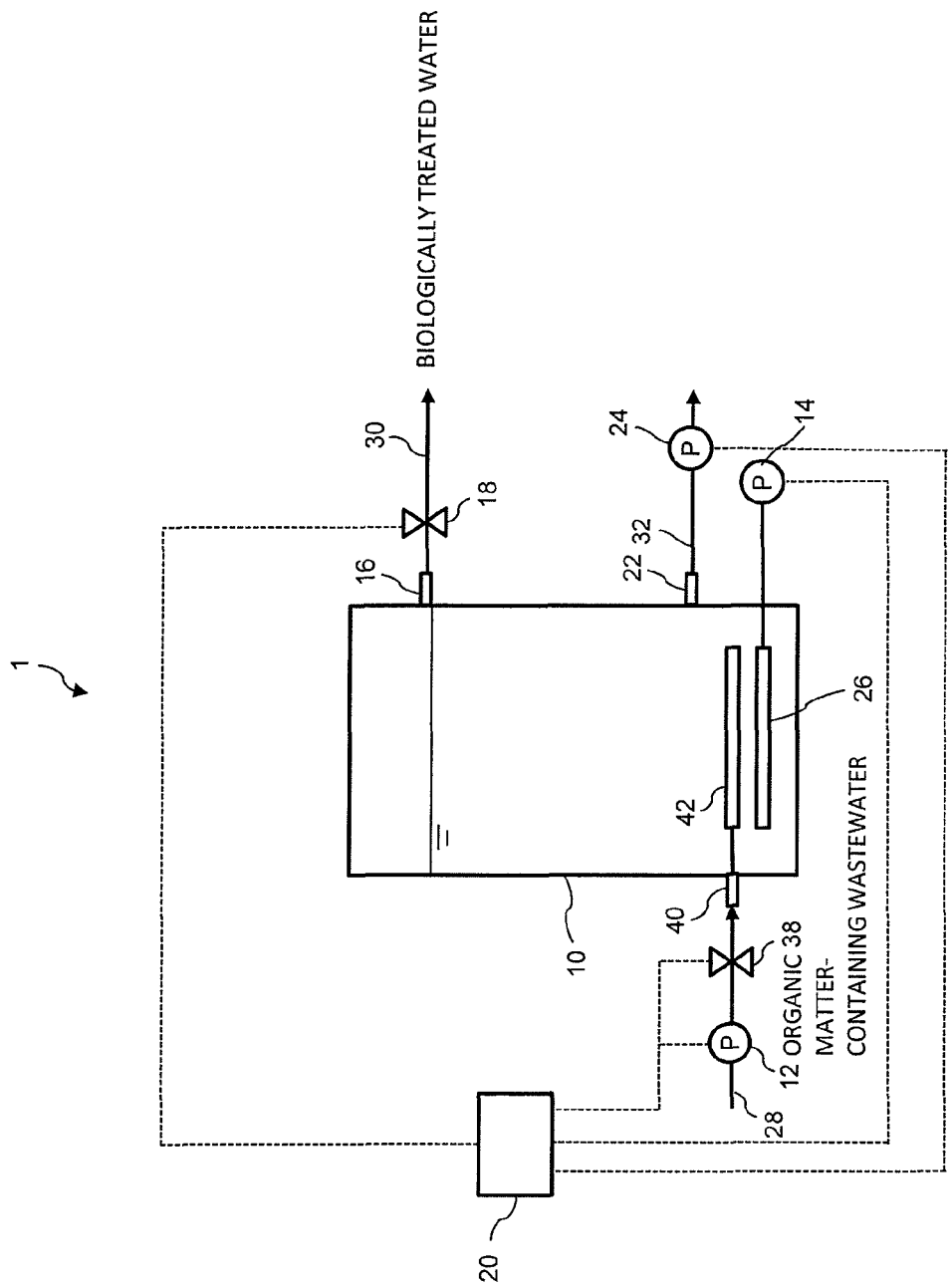
FIG. 5 is a schematic diagram illustrating another example of a device for forming aerobic granules according to an embodiment of the present invention.

Another example of the device for forming aerobic granules according to the present embodiment is shown in FIG. 5. In the granule formation device 1 illustrated in FIG. 5, the wastewater supply line 28 is connected to a wastewater inlet 40 in the lower portion of the semibatch reactor 10 via the wastewater inlet pump 12 and a wastewater inlet valve 38. A wastewater discharge unit 42 is connected to the wastewater inlet 40, and is installed in the lower portion inside the semibatch reactor 10. The biologically treated water outlet 16 of the semibatch reactor 10 is provided above the wastewater inlet 40, and the biologically treated water line 30 is connected to the biologically treated water outlet 16 via the biologically treated water discharge valve 18. The biologically treated water outlet 16 is provided above the wastewater inlet 40, and order to prevent short-cutting of the introduced organic matter-containing wastewater and enable more efficient formation of the granules, is preferably installed as distant as possible from the wastewater inlet 40, and is more preferably installed near the water level in the settling step. The wastewater inlet pump 12, the wastewater inlet valve 38, the biologically treated water discharge valve 18, the sludge withdrawal pump 24 and the aeration pump 14 may each be connected by electrical connection or the like to a control device 20. The remaining configuration is the same as that of the granule formation device 1 of FIG. 1.

In the granule formation device 1 of FIG. 5, in the discharge step (4), by opening the wastewater inlet valve 38 and activating the wastewater inlet pump 12, the organic matter-containing wastewater is supplied from the wastewater inlet 40, through the wastewater supply line 28, and introduced into the semibatch reactor 10 from the wastewater discharge unit 42, thereby discharging the biologically treated water from the biologically treated water outlet 16 and through the biologically treated water line 30. Activation and stopping of the wastewater inlet pump 12, the sludge withdrawal pump 24 and the aeration pump 14, and opening and closing of the wastewater inlet valve 38 and the biologically treated water discharge valve 18 may be controlled by the control device 20.

In this manner, even in the granule formation device 1 of FIG. 5, granules are formed by repeating a cycle composed of three steps, namely an introduction step/discharge step (1), a biological treatment step (2) and a settling step (3).

In the granule formation device 1 of FIG. 5, by discharging the biologically treated water from the biologically treated water outlet 16 by introducing the organic matter-containing wastewater into the semibatch reactor 10, granules having a comparatively small particle size are discharged with the biologically treated water, whereas those granules having a comparatively large particle size are subjected repeatedly to the cycle of steps (1) to (3), enabling more efficient granule formation.

<Method for Treating Wastewater and Device for Treating Wastewater>

A device for treating a wastewater according to this embodiment is provided with a continuous biological treatment tank used for biologically treating an organic matter-containing wastewater with a biological sludge, while the organic matter-containing wastewater is introduced continuously. In the method for treating a wastewater and the device for treating a wastewater according to this embodiment, granules formed by the method for forming aerobic granules described above are supplied to the continuous biological treatment tank used for biologically treating the organic matter-containing wastewater with a biological sludge, while the organic matter-containing wastewater is introduced continuously.

Figure 6:
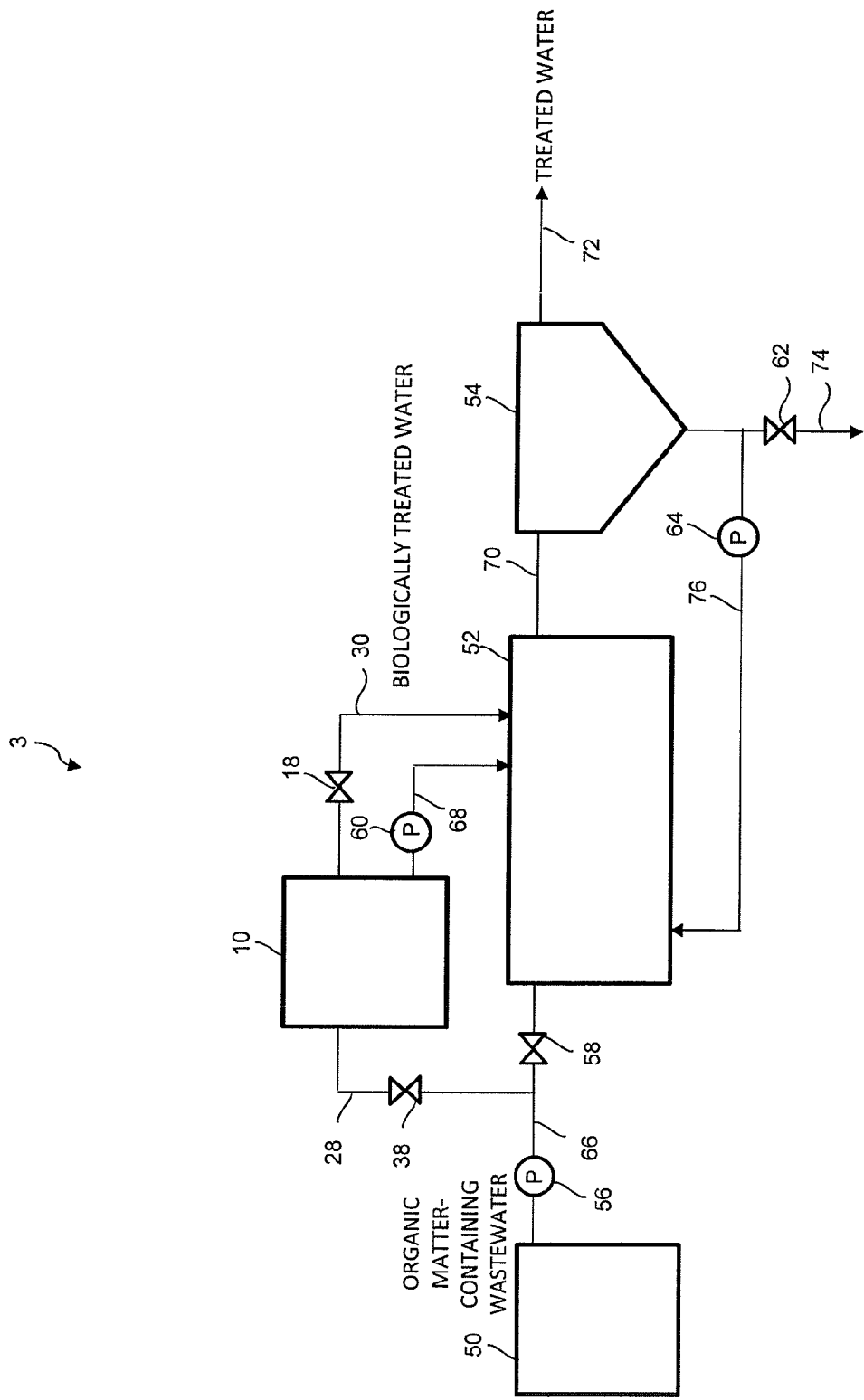
FIG. 6 is a schematic diagram illustrating one example of a device for treating a wastewater according to an embodiment of the present invention.

A schematic diagram illustrating one example of a device for treating a wastewater according to the present embodiment is shown in FIG. 6. The wastewater treatment device 3 includes a wastewater storage tank 50, a semibatch reactor 10, a continuous biological treatment tank 52, and a solid-liquid separator 54.

In the wastewater treatment device 3, an outlet of the wastewater storage tank 50 and a wastewater inlet of the continuous biological treatment tank 52 are connected by a wastewater supply line 66 via a pump 56 and a valve 58. An outlet of the continuous biological treatment tank 52 and an inlet of the solid-liquid separator 54 are connected by a line 70. A treated water line 72 is connected to a treated water outlet of the solid-liquid separator 54. A sludge discharge line 74 is connected to a sludge outlet of the solid-liquid separator 54 via a valve 62, and a portion of the sludge discharge line 74 upstream from the valve 62 and a returned sludge inlet of the continuous biological treatment tank 52 are connected by a sludge return line 76 via a pump 64. A portion of the wastewater supply line 66 between the pump 56 and the valve 58 and a wastewater inlet of the semibatch reactor 10 are connected by a wastewater supply line 28 via a wastewater inlet valve 38. A biologically treated water outlet of the semibatch reactor 10 and a biologically treated water inlet of the continuous biological treatment tank 52 are connected by a biologically treated water line 30 via a biologically treated water discharge valve 18. A sludge outlet of the semibatch reactor 10 and a sludge inlet of the continuous biological treatment tank 52 are connected by a sludge line 68 via a pump 60.

The continuous biological treatment tank 52 includes, for example, a stirring device, an aeration pump, and an aerator or the like connected to the aeration pump, and is configured so that the liquid inside the tank is stirred by the stirring device, and an oxygen-containing gas such as air supplied from the aeration pump passes through the aerator and is supplied into the tank.

The solid-liquid separator 54 is a separation device for separating the biological sludge and the treated water from the biological sludge-containing treated water, and specific examples include separation devices that employ settling separation, pressure flotation, filtration, or membrane separation or the like.

In the wastewater treatment device 3, first, the valve 58 is opened, the pump 56 is activated, and the organic matter-containing wastewater inside the wastewater storage tank 50 is supplied through the wastewater supply line 66 into the continuous biological treatment tank 52. In the continuous biological treatment tank 52, biological treatment of the wastewater using a biological sludge is performed under aerobic conditions (the continuous biological treatment step). The treated water that has been treated in the continuous biological treatment tank 52 is supplied from the outlet of the continuous biological treatment tank 52 to the solid-liquid separator 54 through the line 70. In the solid-liquid separator 54, the biological sludge is separated from the treated water (the solid-liquid separation step). The treated water obtained following the solid-liquid separation passes through the treated water outlet of the solid-liquid separator 54, and is discharged outside the system through the treated water line 72. The biological sludge obtained from the solid-liquid separation is discharged outside the system through the sludge discharge line 74 by opening the valve 62. By activating the pump 64, at least a portion of the biological sludge obtained from the solid-liquid separation may be returned to the continuous biological treatment tank 52 through the sludge return line 76.

When the semibatch reactor 10 is to be operated, the wastewater inlet valve 38 is opened, and at least a portion of the organic matter-containing wastewater inside the wastewater storage tank 50 is supplied to the semibatch reactor 10 through the wastewater supply line 28. In the semibatch reactor 10, by repeatedly performing the aforementioned cycle composed of the introduction step (1), the biological treatment step (2), the settling step (3) and the discharge step (4) (or the cycle composed of the introduction step/discharge step (1), the biological treatment step (2) and the settling step (3)), granules are formed, and by then activating the pump 60, the formed granules can be supplied to the continuous biological treatment tank 52 through the sludge line 68.

The pH in the continuous biological treatment tank 52 is preferably adjusted to a value within a range from 6 to 9 that is appropriate for a typical biological treatment, and is more preferably adjusted to a value within a range from 6.5 to 7.5. The dissolved oxygen (DO) inside the continuous biological treatment tank 52 is typically set to a value of at least 0.5 mg/L that is appropriate for a typical biological treatment, and a concentration of 1 mg/L or higher is particularly desirable.

For the wastewater treatment device 3 illustrated in FIG. 6, a configuration provided with the solid-liquid separator 54 was described as an example, but the solid-liquid separator 54 need not necessarily be provided. However, in terms of factors such as recirculating the granules and improving the wastewater treatment efficiency, it is preferable that the wastewater treatment device 3 includes the solid-liquid separator 54 for separating the biological sludge from the treated water discharged from the continuous biological treatment tank 52, and the sludge return line 76 for returning the biological sludge discharged from the solid-liquid separator 54 to the continuous biological treatment tank 52.

Figure 7:
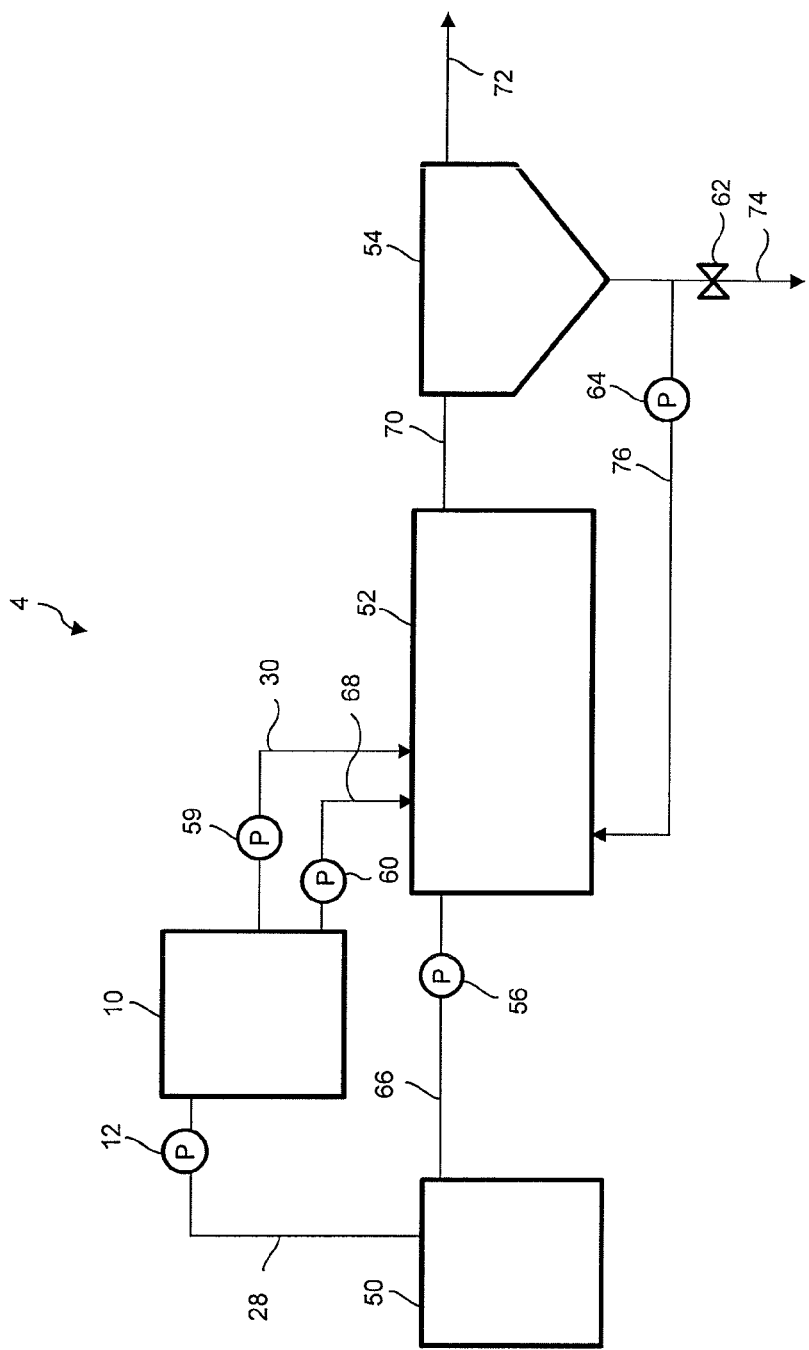
FIG. 7 is a schematic diagram illustrating another example of a device for treating a wastewater according to an embodiment of the present invention.

FIG. 7 is a schematic diagram illustrating another example of a device for treating a wastewater according to an embodiment of the present invention. In the wastewater treatment device 4 illustrated in FIG. 7, those components that are the same as those of the wastewater treatment device 3 illustrated in FIG. 6 are labeled with the same reference signs, and description of those components is omitted. The wastewater treatment device 4 illustrated in FIG. 7 includes a wastewater storage tank 50, a continuous biological treatment tank 52, a semibatch reactor 10, and a solid-liquid separator 54. As described above, the semibatch reactor 10 is a device that forms granules while biologically treating the wastewater. This device forms a granular sludge having a particle size of 200 μm or greater.

In the wastewater treatment device 4, an outlet of the wastewater storage tank 50 and a wastewater inlet of the continuous biological treatment tank 52 are connected by a wastewater supply line 66 via a pump 56. An outlet of the continuous biological treatment tank 52 and an inlet of the solid-liquid separator 54 are connected by a line 70. A treated water line 72 is connected to a treated water outlet of the solid-liquid separator 54. A sludge discharge line 74 is connected to a sludge outlet of the solid-liquid separator 54 via a valve 62, and a portion of the sludge discharge line 74 upstream from the valve 62 and a returned sludge inlet of the continuous biological treatment tank 52 are connected by a sludge return line 76 via a pump 64. An outlet of the wastewater storage tank 50 and a wastewater inlet of the semibatch reactor 10 are connected by a wastewater supply line 28 via a wastewater inlet pump 12. A biologically treated water outlet of the semibatch reactor 10 and a biologically treated water inlet of the continuous biological treatment tank 52 are connected by a biologically treated water line 30 via a pump 59. A sludge outlet of the semibatch reactor 10 and a sludge inlet of the continuous biological treatment tank 52 are connected by a sludge line 68 via a pump 60.

One example of the operation of the wastewater treatment device 4 illustrated in FIG. 7 is described below.

The treatment target wastewater inside the wastewater storage tank 50 is supplied from the wastewater supply line 66 to the continuous biological treatment tank 52 by activating the pump 56. Further, by activating the wastewater inlet pump 12, the wastewater inside the wastewater storage tank 50 is also supplied from the wastewater supply line 28 to the semibatch reactor 10. In the semibatch reactor 10, the wastewater is subjected to biological treatment, while a granular sludge having a particle size of 200 μm or greater is formed. The granular sludge formed inside the semibatch reactor 10 is supplied from the sludge line 68 to the continuous biological treatment tank 52 by activating the pump 60. Further, the treated water inside the semibatch reactor 10 is supplied from the biologically treated water line 30 to the continuous biological treatment tank 52 by activating the pump 59. In the continuous biological treatment tank 52, the wastewater is subjected to biological treatment by the biological sludge containing the granular sludge, for example under aerobic conditions.

The treated water that has been treated in the continuous biological treatment tank 52 is supplied from the line 70 to the solid-liquid separator 54, and the biological sludge is separated from the treated water. By activating the pump 64, the sludge obtained from the solid-liquid separation is returned to the continuous biological treatment tank 52 through the sludge return line 76. Further, by opening the valve 62, the sludge obtained from the solid-liquid separation can be discharged outside the system through the sludge discharge line 74. The treated water inside the solid-liquid separator 54 is discharged outside the system through the treated water line 72.

A more specific description of the treatment conditions and the like for the wastewater treatment device 4 illustrated in FIG. 7 is provided below.

<Treatment Conditions for Continuous Biological Treatment Tank 52>

The amount of BOD load in the wastewater relative to the amount of sludge in the continuous biological treatment tank 52 (the BOD sludge load) is within a range from 0.08 to 0.2 kgBOD/kgMLVSS/d, and is more preferably within a range from 0.1 to 0.18 kgBOD/kgMLVSS/d. If the BOD sludge load is less than 0.08 kgBOD/kgMLVSS/d, then the disintegration rate of the granular sludge supplied from the semibatch reactor 10 tends to be fast, and retaining the granular sludge may become difficult. Further, if the BOD sludge load is greater than 0.2 kgBOD/kgMLVSS/d, then the proportion of flock-like sludge other than the granular sludge inside the tank increases, and bulking (which acts as an obstacle to solid-liquid separation) occurs due to overloading, making it difficult to maintain favorable settling properties. Generally, when the BOD of the wastewater introduced into the continuous biological treatment tank 52 is low, for example 200 mgBOD/L or less, disintegration of the granular sludge becomes more marked, but by performing operations with the BOD sludge load within a range from 0.08 to 0.2 kgBOD/kgMLVSS/d, disintegration of the granules can be suppressed, the settling properties of the sludge inside the continuous biological treatment tank 52 can be maintained at a favorable level, and high-speed treatment of the wastewater is possible. In the present embodiment, even if the BOD concentration of the wastewater introduced into the continuous biological treatment tank 52 is about 50 to 200 mg/L, disintegration of the granular sludge can be suppressed, and high-speed treatment of the wastewater is possible.

The BOD sludge load of the continuous biological treatment tank 52 is adjusted by altering factors such as the flow rate of the wastewater supplied to the continuous biological treatment tank 52, the amount of granular sludge passed through the sludge line 68, and the amount of returned sludge passed through the sludge return line 76. Specifically, based on the BOD of the wastewater supplied to the continuous biological treatment tank 52 and the MLVSS inside the continuous biological treatment tank 52, the flow rate of the wastewater, the granular sludge supply rate and the amount of returned sludge, and the amount of excess sludge discharged are adjusted so that the BOD sludge load of the continuous biological treatment tank 52 satisfies the range described above. From the viewpoint of ease of operation, adjustment of the BOD sludge load is preferably performed by adjusting the flow rate of the wastewater supplied to the continuous biological treatment tank 52, but adjustment may also be made by altering the amount of sludge within the system.

Adjustment of the wastewater flow rate and the amounts of granular sludge and returned sludge may be performed by an operator by adjusting the output of each of the pumps, or may be performed by using a control device that controls the output of each pump based on the BOD value of the wastewater and the MLVSS value. The BOD value of the wastewater supplied to the continuous biological treatment tank 52 may, for example, be either measured by an operator in accordance with the official method, or estimated from daily measured TOC and COD values. Further, the MLVSS inside the continuous biological treatment tank 52 may, for example, be either measured by an operator in accordance with the official method, or estimated from the value from an MLSS meter installed in the continuous biological treatment tank 52, and the average MLVSS/MLSS ratio derived from daily measurements.

The actual hydraulic retention time (actual HRT) in the continuous biological treatment tank 52 is preferably within a range from 5 hours to 10 hours, and is more preferably within a range from 5 hours to 8 hours. The actual HRT refers to the HRT value calculated from the combined flow rate obtained by adding the wastewater flow rate of the introduced wastewater (in FIG. 7, the flow rate of the wastewater passing through the wastewater supply line 66) and the sludge flow rate due to sludge recirculation (in FIG. 7, the flow rate of sludge passing through the sludge return line 76), and the volume of the continuous biological treatment tank 52. If the actual HRT exceeds 10 hours, then compared with the case when the HRT is within the range from 5 to 10 hours, the granular sludge can sometimes be more prone to disintegration. Further, if the retention time of the granular sludge in the inside the continuous biological treatment tank 52 is less than 5 hours, then compared with the case of a retention time within the range from 5 to 10 hours, the generation of flock-like sludge in the tank tends to increase, the organic matter concentration inside the tank falls, and retaining the granular sludge can sometimes become difficult.

The MLSS concentration inside the continuous biological treatment tank 52 is preferably maintained at 3,000 mg/L or greater, and is more preferably maintained at 4,000 mg/L or greater. In activated sludge treatment in those cases where the organic matter concentration in the wastewater is low, such as typical sewage, because of the difficulty in settling and separating the sludge, the MLSS concentration is often maintained at about 1,000 to 2,000 mg/L, but in the treatment device of the present embodiment, even if operation is conducted at an MLSS concentration of 3,000 mg/L or greater, the sludge concentration in the system can be maintained at a high level, while retaining a sludge having superior settling properties, meaning high-speed treatment of the wastewater is possible. As a result, the continuous biological treatment tank 52 can be substantially reduced in size, enabling considerable space saving in terms of the site area required for the wastewater treatment facility, and a significant reduction in equipment costs.

The pH inside the continuous biological treatment tank 52 is preferably adjusted to a value within a range from 6 to 9 that is appropriate for a typical biological treatment, and is more preferably adjusted to a value within a range from 6.5 to 7.5. If the pH is outside this range, then an acid or alkali is preferably used to adjust the pH.

<Formation of Granular Sludge in Semibatch Reactor 10>

In the semibatch reactor 10, granules are formed by repeating the aforementioned cycle composed of the introduction step (1), the biological treatment step (2), the settling step (3) and the discharge step (4) (or alternatively, the cycle composed of the introduction step/discharge step (1), the biological treatment step (2) and the settling step (3)), and these granules are supplied to the continuous biological treatment tank 52.

In the introduction step, the wastewater supplied to the semibatch reactor 10 need not necessarily be the same wastewater as that supplied to the continuous biological treatment tank 52, and a wastewater from a separate system or the like may be supplied to the semibatch reactor 10. However, in terms of forming a granular sludge having microbial flora appropriate for the treatment target wastewater, it is preferable that a portion of the wastewater being supplied to the continuous biological treatment tank 52 is diverted and introduced into the semibatch reactor 10, with this wastewater being used for forming the granules.

The granular sludge inside the semibatch reactor 10 need not necessarily be supplied directly to the continuous biological treatment tank 52. For example, in those cases where the sludge in the solid-liquid separator 54 is returned to the continuous biological treatment tank 52, the granular sludge inside the semibatch reactor 10 may be introduced into the solid-liquid separator 54, and then fed into the sludge return line 76 for returning the sludge from the solid-liquid separator 54 to the continuous biological treatment tank 52. Any configuration the enables the granular sludge inside the semibatch reactor 10 to be supplied to the continuous biological treatment tank 52 may be used.

The treated water discharged from the semibatch reactor 10 may be supplied to the continuous biological treatment tank 52, may be supplied to the solid-liquid separator 54, or may be discharged from the system as final treated water, but in those cases where the water discharged from the semibatch reactor 10 still contains residual components such as BOD or nitrogen compounds, in order to ensure no deterioration in the final treated water, the discharged water is preferably supplied to the continuous biological treatment tank 52.

In terms of the properties of the sludge inside the semibatch reactor 10, sludge particles having a particle size of 200 μm or greater preferably exist in an amount that represents at least 50% of the total volume of sludge, and more preferably 85% or more of the total volume of sludge. The particle size of the granular sludge and the volume distribution of the various particle sizes are measured using a laser diffraction particle size distribution analyzer.

Supply of the granular sludge from the semibatch reactor 10 may be performed during the biological treatment step (2), during the settling step (3), or during the discharge step (4). The granular sludge formed in the semibatch reactor 10 is a sludge formed as a result of self-granulation, and is, for example, a biological sludge having an average particle size of 200 μm or greater. Further, in the present embodiment, whether or not a granular sludge has been formed can be ascertained by measuring the particle size distribution of the sludge inside the semibatch reactor 10, and when the average particle size reaches a value of 200 μm or greater, a granular sludge can be deemed to have formed. Alternatively, the SVI value of the sludge in the semibatch reactor 10 may be measured regularly using a settling properties test, and when the SVI5 value calculated from the volume proportions obtained after settling for 5 minutes reaches a specified value or lower (for example, not more than 80 mL/g), a granular sludge can be deemed to have formed (and the smaller the SVI value and the larger the average particle size, the more favorable the granular sludge).

The pH in the semibatch reactor 10 is preferably adjusted to a value within a range from 6 to 9 that is appropriate for a typical biological treatment, and is more preferably adjusted to a value within a range from 6.5 to 7.5. If the pH value is outside this range, then an acid or alkali or the like is preferably used to adjust the pH. In those cases where a pH adjustment is performed in the semibatch reactor 10, in terms of enabling appropriate measurement of the pH, the pH adjustment is preferably performed while the contents of the semibatch reactor 10 are being stirred, rather than in a state in which no stirring is occurring. The dissolved oxygen (DO) inside the semibatch reactor 10 is typically set to a value of at least 0.5 mg/L that is appropriate for a typical biological treatment, and a concentration of 1 mg/L or higher is particularly desirable.

If the reactor volume of the semibatch reactor 10 is too small relative to the volume of the continuous biological treatment tank 52, then increasing the volume of granules inside the tank is slow, and considerable time is required at startup. Accordingly, the reactor volume is preferably not more than ⅓, and more preferably ⅕ or less, relative to the volume of the continuous biological treatment tank 52. Further, the reactor volume of the semibatch reactor 10 is preferably at least 1/20 of the volume of the continuous biological treatment tank 52.

Figure 8:
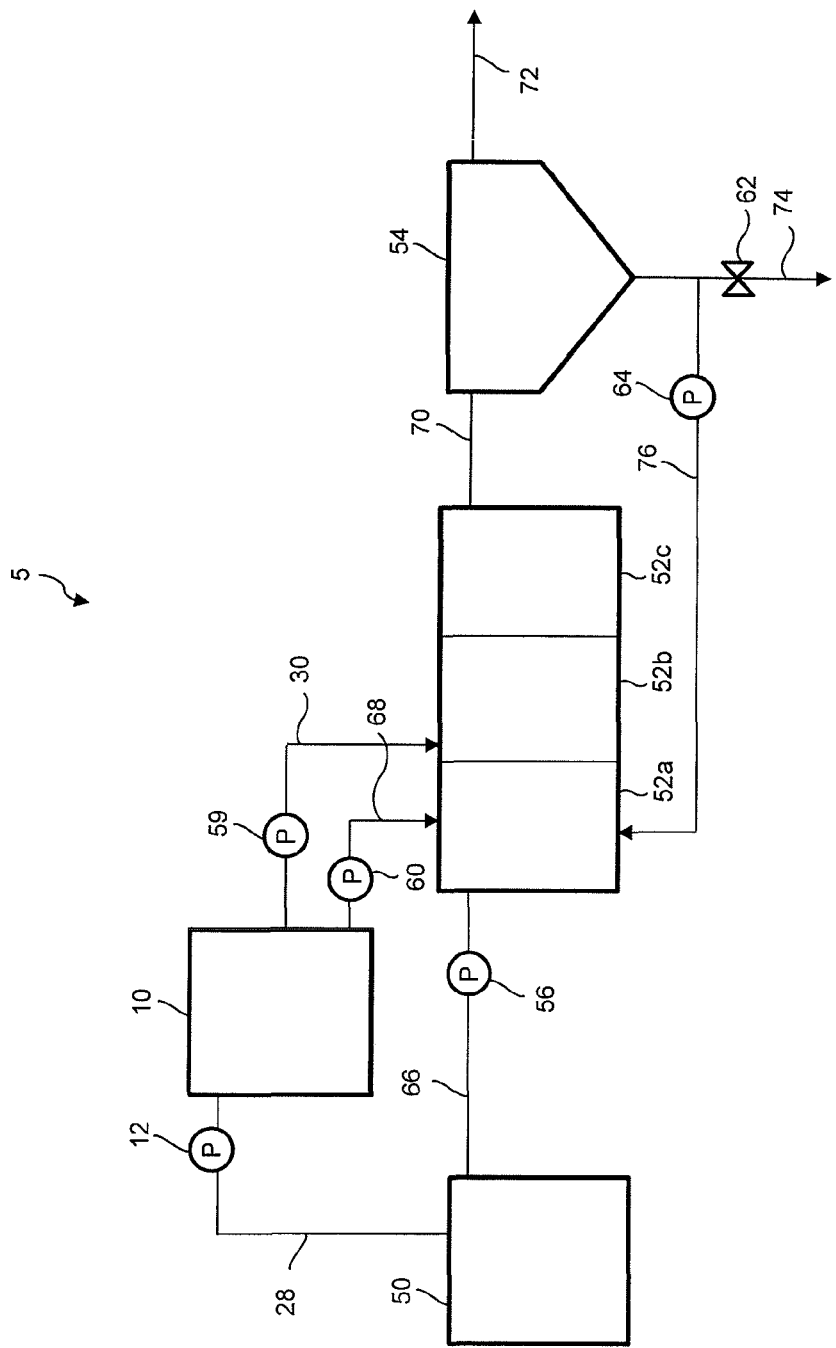
FIG. 8 is a schematic diagram illustrating another example of a device for treating a wastewater according to an embodiment of the present invention.

FIG. 8 is a schematic diagram illustrating another example of a device for treating a wastewater according to an embodiment of the present invention. In the wastewater treatment device 5 illustrated in FIG. 8, those components that are the same as those of the wastewater treatment device 4 illustrated in FIG. 7 are labeled with the same reference signs, and description of those components is omitted. The wastewater treatment device 5 illustrated in FIG. 8 includes three continuous biological treatment tanks (52a, 52b, 52c). In the wastewater treatment device 5 illustrated in FIG. 8, one end of the sludge line 68 is connected to the sludge outlet of the semibatch reactor 10, and the other end is connected to a sludge supply port of the continuous biological treatment tank 52a. One end of the biologically treated water line 30 is connected to the treated water outlet of the semibatch reactor 10, and the other end is connected to a treated water inlet of the continuous biological treatment tank 52b.

In the case of a single continuous biological treatment tank, because the wastewater is in a totally mixed state, the organic matter concentration inside the tank is constant, but by installing multiple continuous biological treatment tanks, as illustrated in FIG. 8, a difference develops in the organic matter concentration inside each tank, and therefore compared with the case of a single continuous biological treatment tank, a satiated state and a starved state can be formed more easily for the microbes inside the tank, thereby better suppressing disintegration of the granular sludge. Further, by installing multiple continuous biological treatment tanks, the microbes can multiply using the granular sludge inside the tank as nuclei, and the proportion of granular sludge inside the continuous biological treatment tanks can be increased.

When multiple continuous biological treatment tanks are installed, the BOD sludge load of the combined continuous biological treatment tanks is preferably within a range from 0.08 to 0.2 kgBOD/kgMLVSS/d. In other words, provided the BOD sludge load of the combined continuous biological treatment tanks is within a range from 0.08 to 0.2 kgBOD/kgMLVSS/d, the BOD sludge load of each continuous biological treatment tank need not necessarily satisfy the above range. When multiple continuous biological treatment tanks are installed, in terms of suppressing the disintegration of the granular sludge and the like, it is preferable that the BOD sludge load of the combined continuous biological treatment tanks is within a range from 0.08 to 0.2 kgBOD/kgMLVSS/d, and that the BOD sludge load of each tank decreases in order from the first-stage continuous biological treatment tank to the last-stage continuous biological treatment tank. In this case, it is even more preferable that the BOD sludge load of the first-stage continuous biological treatment tank is within a range from 0.24 to 0.6 kgBOD/kgMLVSS/d, and the BOD sludge load of the final-stage continuous biological treatment tank is within a range from 0.02 to 0.05 kgBOD/kgMLVSS/d. Adjustment of the BOD sludge load within each tank can be performed by dividing the wastewater for introduction into each tank, and adjusting the respective flow rates as appropriate.

Figure 9:
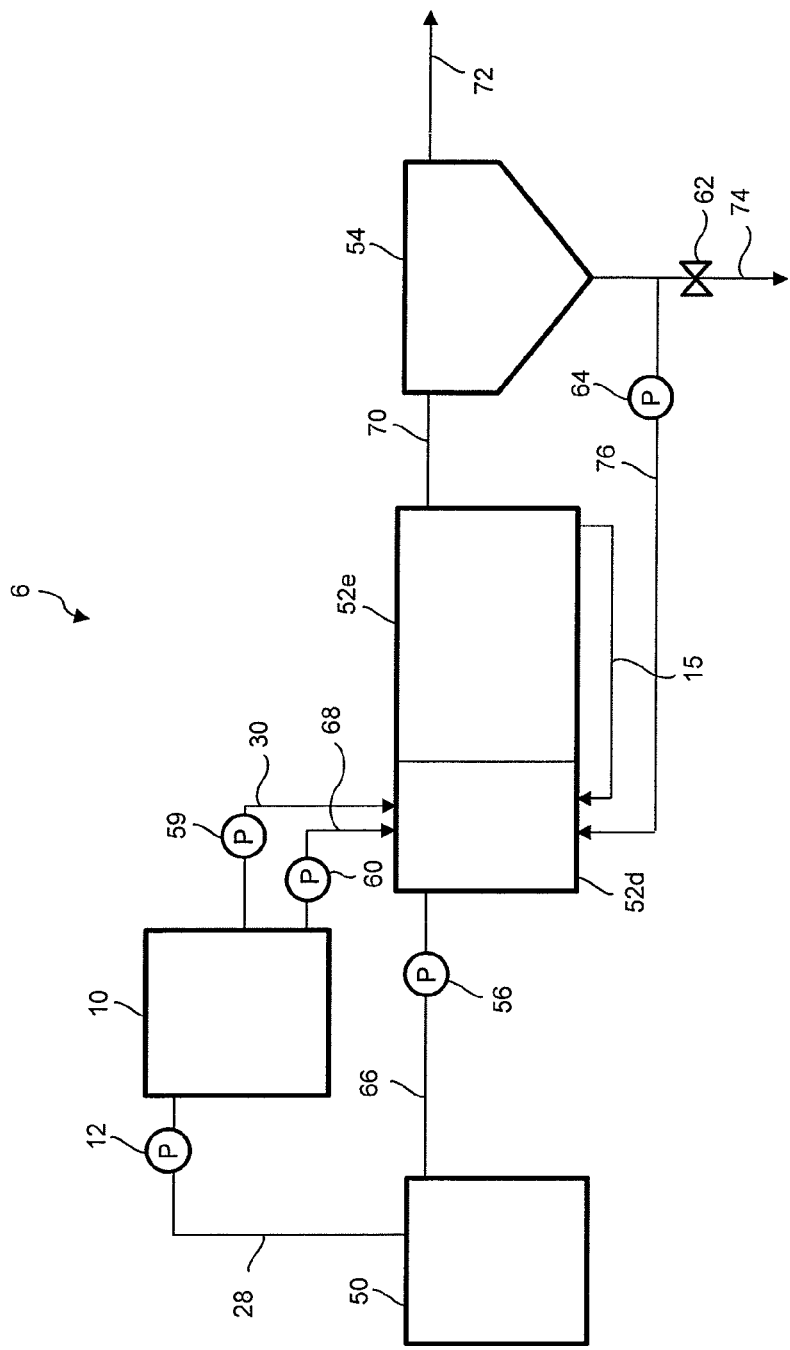
FIG. 9 is a schematic diagram illustrating another example of a device for treating a wastewater according to an embodiment of the present invention.

FIG. 9 is a schematic diagram illustrating another example of a device for treating a wastewater according to an embodiment of the present invention. In the wastewater treatment device 6 illustrated in FIG. 9, those components that are the same as those of the wastewater treatment device 4 illustrated in FIG. 7 are labeled with the same reference signs, and description of those components is omitted. The wastewater treatment device 6 illustrated in FIG. 9 is suited to the treatment of wastewater containing mainly nitrogen compounds, and includes a continuous biological treatment tank composed of a first-stage anoxic tank 52d and a second-stage aeration tank 52e. Here, the term "anoxic tank" describes a reaction tank in which anoxic conditions are maintained inside the tank, and "anoxic conditions" describes conditions in which dissolved oxygen does not exist in the wastewater, but oxygen derived from nitrites or nitrates does exist.

In the continuous biological treatment tank illustrated in FIG. 9, nitrogen compounds and organic matter in the wastewater are treated by a recirculating nitrification-denitrification method. Specifically, in the second-stage aeration tank 52e, the nitrogen-containing substances in the wastewater are subjected to an oxidation treatment under aerobic conditions and converted to nitrite nitrogen or nitrate nitrogen. A recirculation line 15 provided between the aeration tank 52e and the anoxic tank 52d is used to supply a sludge mixed liquid containing the nitrite nitrogen or nitrate nitrogen from the second-stage aeration tank 52e to the first-stage anoxic tank 52d. In the anoxic tank 52d, the nitrite nitrogen or nitrate nitrogen undergoes a reduction treatment under anoxic conditions to form nitrogen gas.

Because the particle size of the granular sludge supplied to the continuous biological treatment tank is large, organic matter oxidizing bacteria and nitrifying bacteria may exist on the outside of the sludge particles, with denitrifying bacteria existing comparatively inside the sludge particles. As a result, in a treatment device in which the continuous biological treatment tank 52 is composed of the anoxic tank 52d and the aeration tank 52e, by supplying a granular sludge having a particle size of 200 μm or greater to the continuous biological treatment tank, nitrogen compounds and organic matter can be treated efficiently by the granular sludge. Further, by including an anoxic step in the continuous biological treatment tank, the denitrifying bacteria that constitute part of the granular sludge can be retained inside the granules, and the granules can be better maintained in the continuous biological treatment tank. Further, by supplying a granular sludge having a particle size of 200 μm or greater to a continuous biological treatment tank composed of the anoxic tank 52d and the aeration tank 52e, and ensuring that the BOD sludge load of the overall continuous biological treatment tank (the total BOD load of the anoxic tank 52d and the aeration tank 52e) is within a range from 0.08 to 0.2 kgBOD/kgMLVSS/d, disintegration of the granular sludge can be better suppressed, and the granular sludge can be maintained and grown inside the tank. Setting the BOD sludge load of the overall continuous biological treatment tank to a value within a range from 0.08 to 0.2 kgBOD/kgMLVSS/d, and the BOD sludge load of the anoxic tank 52d to a value within a range from 0.16 to 0.6 kgBOD/kgMLVSS/d is particularly desirable.

Figure 10:
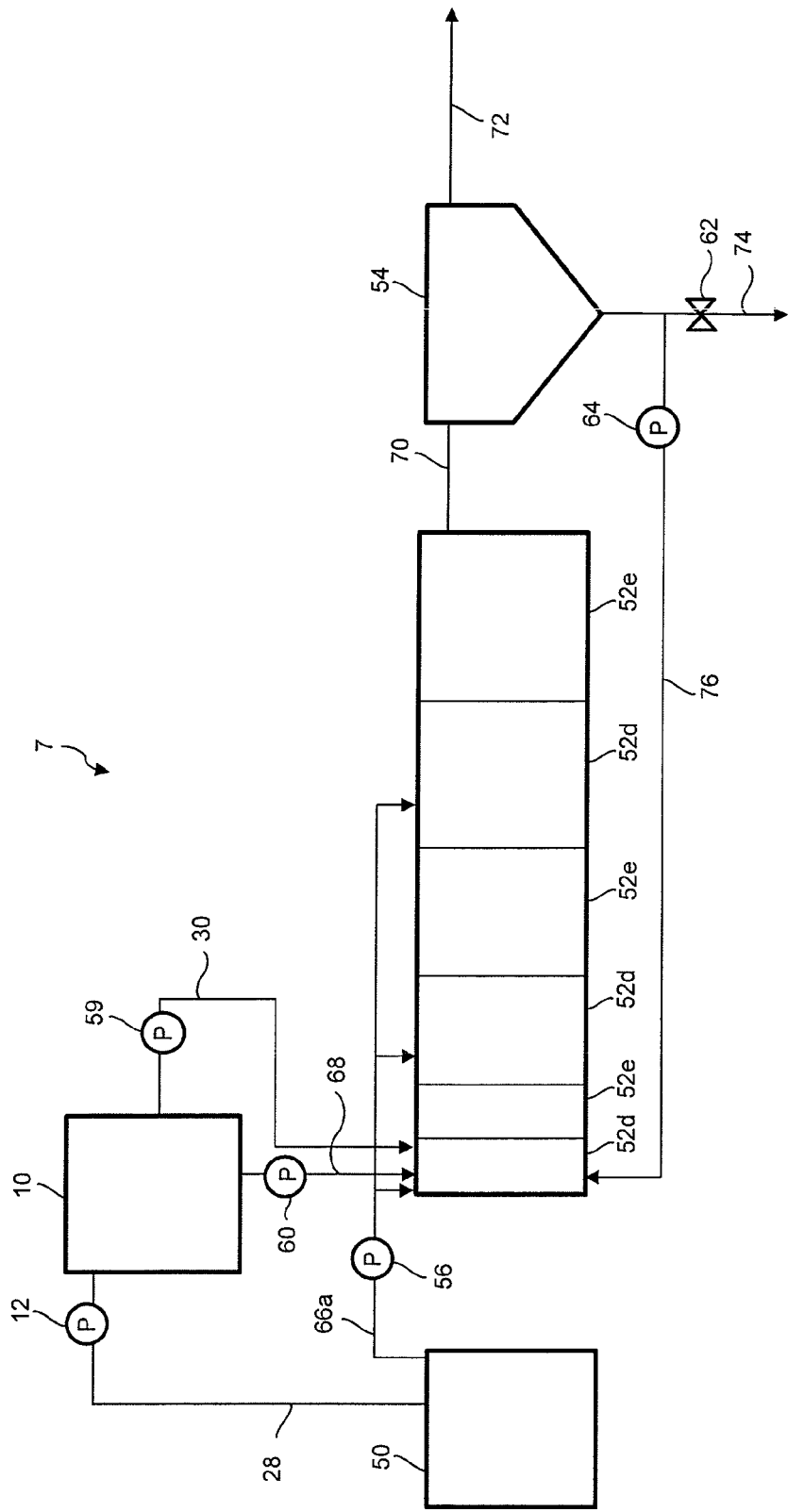
FIG. 10 is a schematic diagram illustrating another example of a device for treating a wastewater according to an embodiment of the present invention.

FIG. 10 is a schematic diagram illustrating another example of a device for treating a wastewater according to an embodiment of the present invention. In the wastewater treatment device 7 illustrated in FIG. 10, those components that are the same as those of the wastewater treatment device 4 illustrated in FIG. 7 are labeled with the same reference signs, and description of those components is omitted. The wastewater treatment device 7 illustrated in FIG. 10 includes a continuous biological treatment tank in which multiple anoxic tanks 52d and aeration tanks 52e are provided in an alternating arrangement. The continuous biological treatment tank illustrated in FIG. 10 employs a system in which a wastewater supply line 66a is connected to each of the anoxic tanks 52d (namely, a step-feed multistage nitrification-denitrification process). In each anoxic tank 52d and each aeration tank 52e, nitrogen compounds undergo a nitrification-denitrification treatment and are converted to nitrogen gas.

Because the particle size of the granular sludge supplied to the continuous biological treatment tank is large, organic matter oxidizing bacteria and nitrifying bacteria may exist on the outside of the sludge particles, with denitrifying bacteria existing comparatively inside the sludge particles. As a result, in a treatment device in which the continuous biological treatment tank is composed of the anoxic tanks 52d and the aeration tanks 52e, by supplying a granular sludge having a particle size of 200 μm or greater to the continuous biological treatment tank, nitrogen compounds and organic matter can be treated efficiently by the granular sludge. Further, by including an anoxic step in the continuous biological treatment tank, the denitrifying bacteria that constitute part of the granular sludge can be retained inside the granules, and the granules can be better maintained in the continuous biological treatment tank. In the wastewater treatment device 7 shown in FIG. 10, the BOD sludge load of the overall continuous biological treatment tank (the total BOD load of each anoxic tank 52d and each aeration tank 52e) is within a range from 0.08 to 0.2 kgBOD/kgMLVSS/d. Setting the BOD sludge load of the anoxic tanks 52d to a value within a range from 0.16 to 0.6 kgBOD/kgMLVSS/d is particularly desirable.

Figure 11:
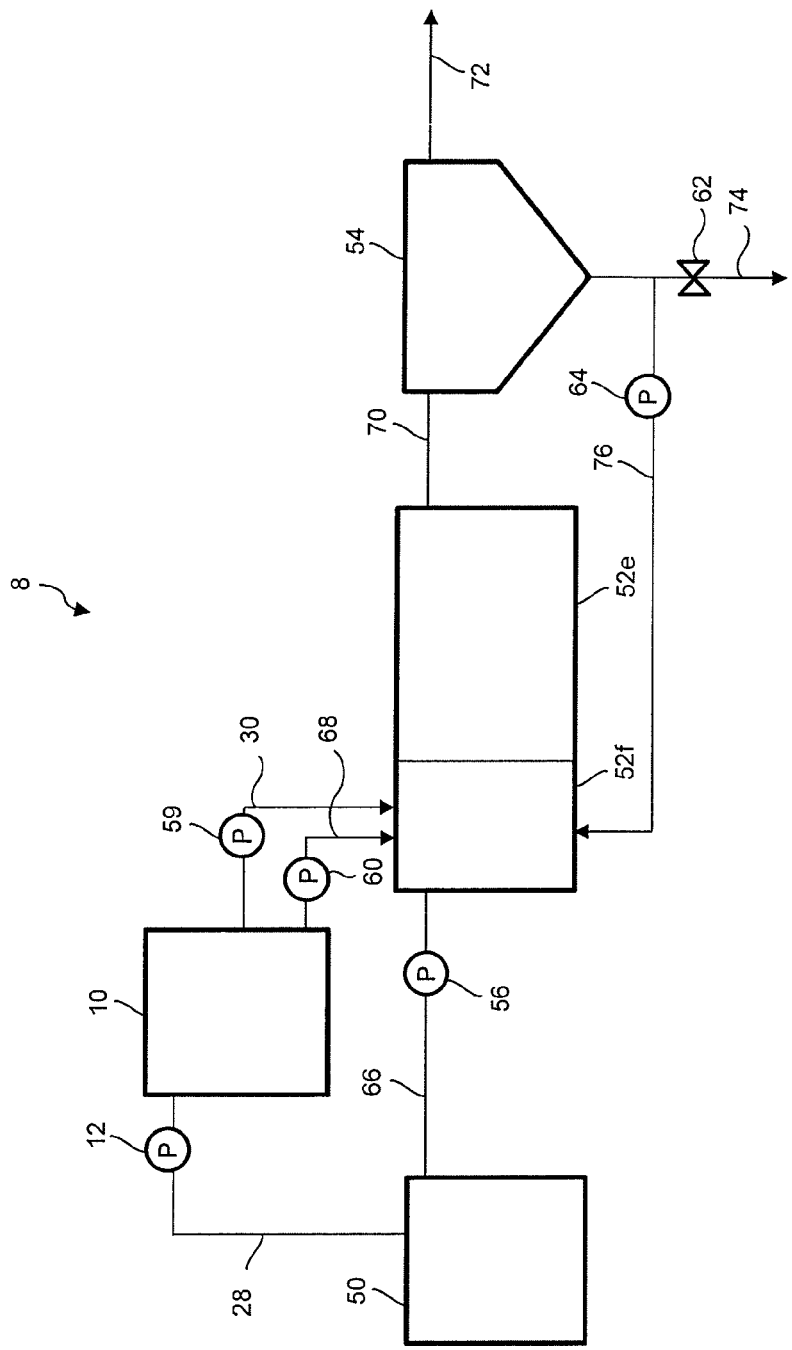
FIG. 11 is a schematic diagram illustrating another example of a device for treating a wastewater according to an embodiment of the present invention.

FIG. 11 is a schematic diagram illustrating another example of a device for treating a wastewater according to an embodiment of the present invention. In the wastewater treatment device 8 illustrated in FIG. 11, those components that are the same as those of the wastewater treatment device 4 illustrated in FIG. 7 are labeled with the same reference signs, and description of those components is omitted. The wastewater treatment device 8 illustrated in FIG. 11 is suited to the treatment of wastewater containing mainly phosphorus compounds, and includes a continuous biological treatment tank composed of a first-stage anaerobic tank 52f and a second-stage aeration tank 52e (namely, a continuous biological treatment tank using a so-called AO process (Anaerobic-Oxic process)). In the continuous biological treatment tank shown in FIG. 11, phosphorus compounds and organic matter in the wastewater are both treated by the AO process (Anaerobic-Oxic process). Here, the term "anaerobic tank" describes a reaction tank in which anaerobic conditions are maintained inside the tank, meaning not only does dissolved oxygen not exist in the wastewater, but oxygen derived from nitrites and nitrates also does not exist.

Because the particle size of the granules supplied to the continuous biological treatment tank is large, organic matter oxidizing bacteria may exist on the outside of the sludge particles, with bacteria that are capable of metabolizing and removing phosphorus under anaerobic conditions and aerobic conditions (phosphorus accumulating bacteria) existing inside the sludge particles. As a result, in a treatment device having a continuous biological treatment tank composed of the anaerobic tank 52f and the aeration tank 52e, by supplying granular sludge having a particle size of 200 μm or greater to the continuous biological treatment tank, phosphorus compounds and organic matter can be treated efficiently by the granular sludge. Further, by including an anaerobic step and an aeration step in the continuous biological treatment tank, the phosphorus accumulating bacteria that exist in the interior of the granular sludge can be retained inside the granules, and the granules can be maintained without disintegration in the continuous biological treatment tank. By supplying the granular sludge having a particle size of 200 μm or greater to the continuous biological treatment tank composed of the anaerobic tank 52f and the aeration tank 52e, as well as ensuring that the BOD sludge load of the overall continuous biological treatment tank (the total BOD load of the anaerobic tank 52f and the aeration tank 52e) is within a range from 0.08 to 0.2 kgBOD/kgMLVSS/d, disintegration of the granular sludge can be suppressed even better, and the granular sludge can be maintained and grown inside the tank. Setting the BOD sludge load of the overall continuous biological treatment to a value within a range from 0.08 to 0.2 kgBOD/kgMLVSS/d, and the BOD sludge load of the anaerobic tank 52f to a value within a range from 0.16 to 0.6 kgBOD/kgMLVSS/d is particularly desirable.

Although omitted in the figure, the continuous biological treatment tank illustrated in FIG. 11 may also be a continuous biological treatment tank that has an anaerobic tank, an anoxic tank and an aeration tank arranged in series, and employs a process in which a sludge mixed liquid containing nitrate nitrogen in the aeration tank is recirculated into the anoxic tank (a so-called A2O process (Anaerobic-Anoxic-Oxic process).

Figure 12:
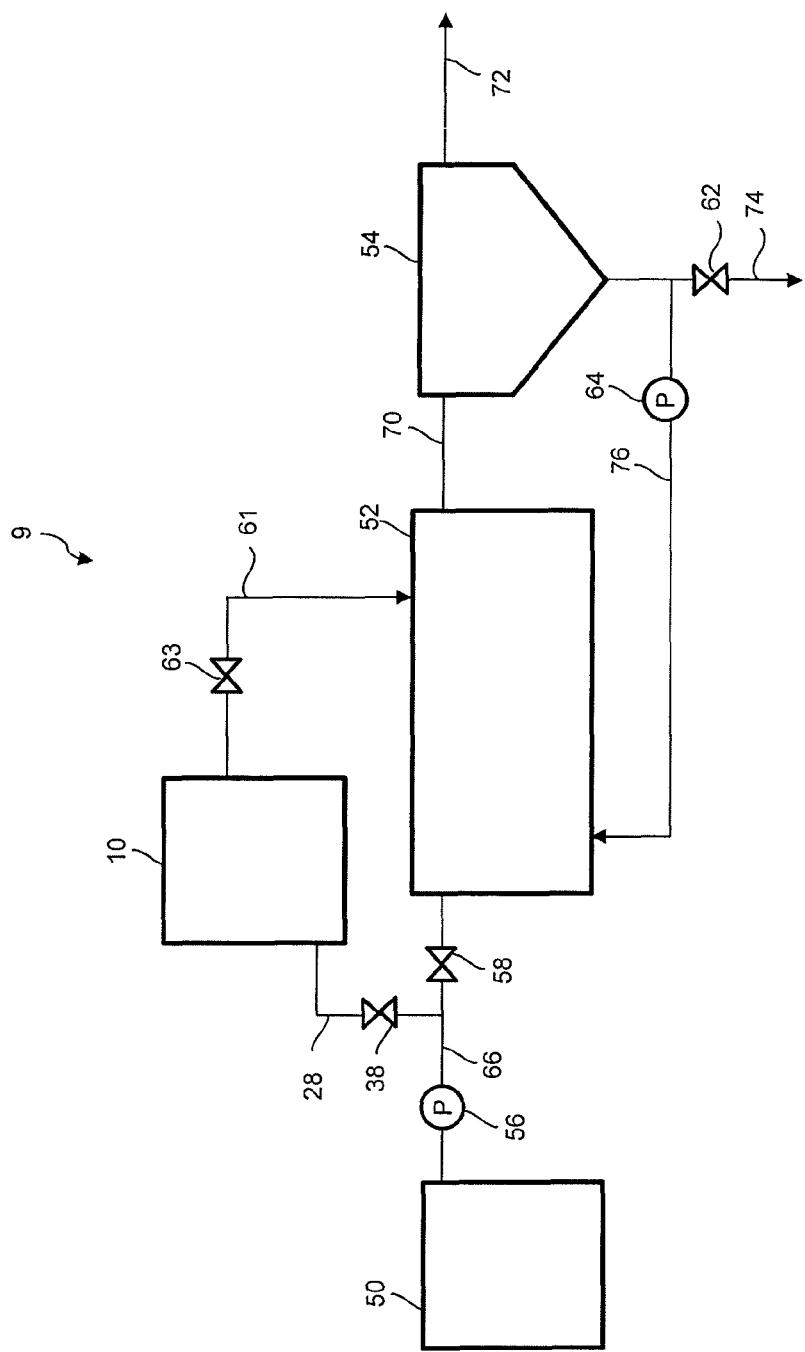
FIG. 12 is a schematic diagram illustrating another example of a device for treating a wastewater according to an embodiment of the present invention.

FIG. 12 is a schematic diagram illustrating another example of a device for treating a wastewater according to an embodiment of the present invention. In the wastewater treatment device 9 illustrated in FIG. 12, those components that are the same as those of the wastewater treatment device 4 illustrated in FIG. 7 are labeled with the same reference signs, and description of those components is omitted. In the wastewater treatment device 9 illustrated in FIG. 12, a pump 56 and a valve 58 are provided in the wastewater supply line 66, and a wastewater inlet valve 38 is provided in the wastewater supply line 28. One end of the wastewater supply line 28 is connected to the wastewater supply line 66 at a position between the pump 56 and the valve 58, and the other end is connected to the wastewater inlet of the semibatch reactor 10. Further, the wastewater treatment device 9 shown in FIG. 12 also has a sludge and treated water supply line 61 that supplies the treated water and the granular sludge discharged from the semibatch reactor 10 to the continuous biological treatment tank 52. A valve 63 is provided in this sludge and treated water supply line 61. The sludge and treated water supply line 61 has the function of a treated water supply device that supplies the treated water discharged from the semibatch reactor 10 to the continuous biological treatment tank 52, and the function of a sludge supply device that supplies the granular sludge to the continuous biological treatment tank 52.

Figure 13:
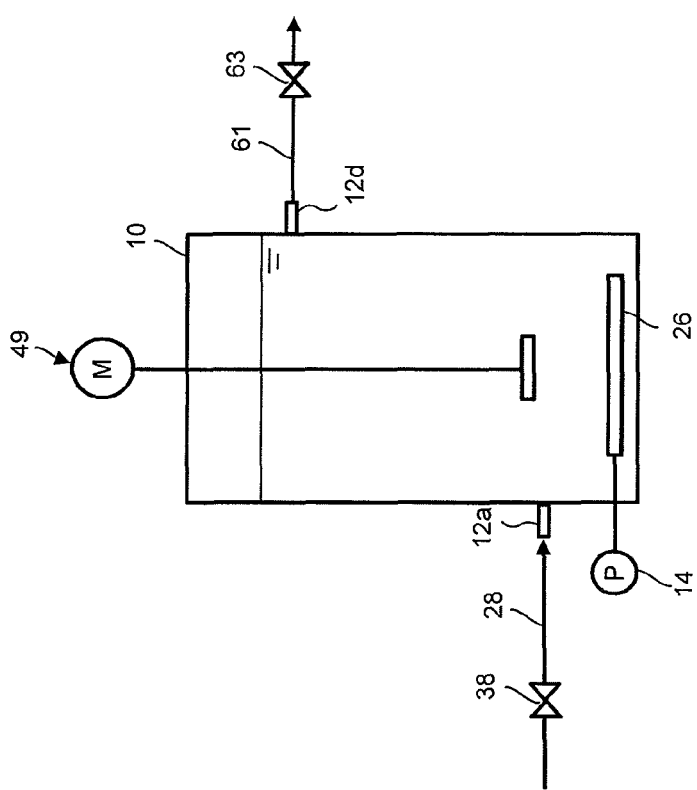
FIG. 13 is a schematic diagram illustrating one example of the structure of a semibatch biological treatment tank used in the device for treating a wastewater illustrated in FIG. 12.
Figure 14:
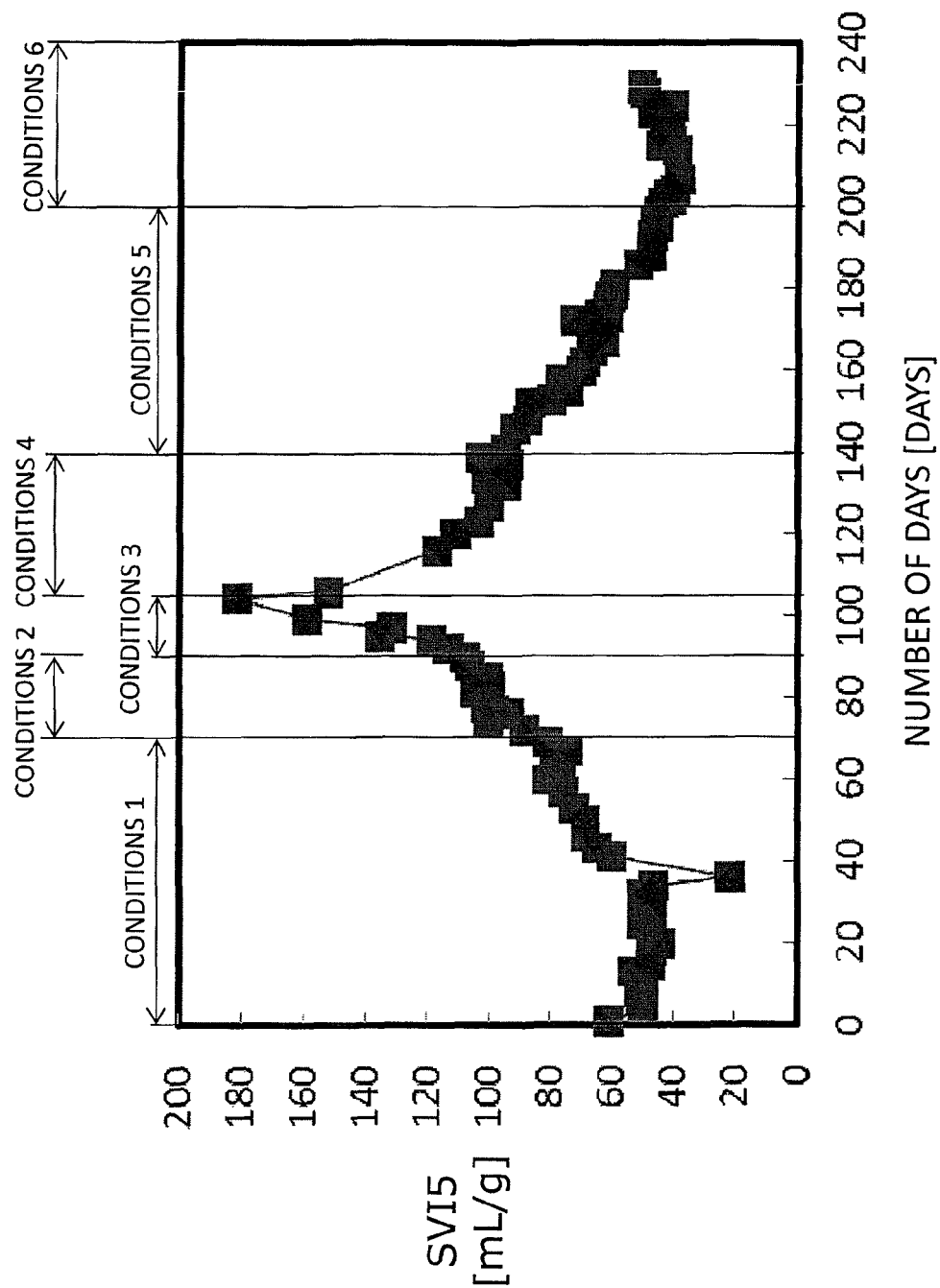
FIG. 14 is a diagram illustrating the change over time in SVI5 in Example 1 and Comparative Example 1.

FIG. 13 is a schematic diagram illustrating one example of the structure of a semibatch biological treatment tank used in the device for treating a wastewater illustrated in FIG. 12. The semibatch reactor 10 illustrated in FIG. 13 is provided with a treated water outlet 12d for discharging the treated water and granular sludge, and one end of the sludge and treated water supply line 61 is connected to this treated water outlet 12d. The other end of the sludge and treated water supply line 61 is connected to the continuous biological treatment tank 52. In the semibatch reactor 10 illustrated in FIG. 13, a wastewater inlet 12a through which the wastewater is introduced is provided at a lower position than the treated water outlet 12d.

In the semibatch reactor 10 shown in FIG. 13, introduction of the wastewater and discharge of the treated water are performed simultaneously. In other words, the steps of introduction of the wastewater and discharge of the treated water, biological treatment of the treatment target substances, and settling of the biological sludge are performed repeatedly. One example of the operation of the semibatch reactor 10 illustrated in FIG. 13, together with the operation of the wastewater treatment device illustrated in FIG. 12, is described below.

First, the pump 56 is activated and the valve 58 is opened, and the treatment target wastewater in the wastewater storage tank 50 is supplied continuously from the wastewater supply line 66 to the continuous biological treatment tank 52. Following biological treatment of the wastewater in the continuous biological treatment tank 52, the treated water is supplied from the line 70 to the solid-liquid separator 54. When the semibatch reactor 10 is to be operated, the valve 38 and the valve 63 are opened, and wastewater is supplied from the wastewater supply line 28 to the semibatch reactor 10, while the treated water and granular sludge inside the semibatch reactor 10 is supplied from the sludge and treated water supply line 61 to the continuous biological treatment tank 52 (wastewater introduction/treated water discharge). By operating a stirring device 49 during this process, the granular sludge inside the semibatch reactor 10 can be supplied efficiently from the sludge and treated water supply line 61 to the continuous biological treatment tank 52. Once the granular sludge having a particle size of 200 μm or greater has been supplied to the biological sludge inside the continuous biological treatment tank 52, the valve 38 and the valve 63 are closed. Then, with the stirring device 49 still operating, the aeration pump 14 is activated, air supply into the semibatch reactor 10 is started, and biological treatment of the wastewater is performed (the biological treatment step).

After a prescribed time has passed, operation of the aeration pump 14 is stopped, thereby stopping supply of air, and the stirring device 49 is also stopped (completion of the biological treatment step). Following completion of the biological treatment, the biological sludge inside the semibatch reactor 10 is left to settle for a specified time, thereby separating the contents of the semibatch reactor 10 into a biological sludge and a treated water (biological sludge settling). The process then returns to the wastewater introduction/treated water discharge step.

In this embodiment, because the wastewater inlet 12a provided in the semibatch reactor 10 is located at a lower position than the treated water outlet 12d, the wastewater introduced into the semibatch reactor 10 is prevented from being discharged from the semibatch reactor 10 without undergoing biological treatment (wastewater short-cut). As a result, a granular sludge can be formed efficiently in the semibatch reactor 10. Further, the treated water from inside the semibatch reactor 10 is discharged by being pushed upward by the introduced wastewater, meaning biological sludge with poor settling properties (such as ungranulated sludge) can be proactively discharged from the system. As a result, biological sludge with superior settling properties tends to remain inside the semibatch reactor 10, enabling even more efficient formation of the granular sludge.

During formation of the granular sludge in the semibatch biological treatment tank, it is desirable to appropriately control the settling time and the wastewater introduction rate per batch. The settling time for allowing the sludge to settle following stopping of the stirring (including stirring by aeration) is calculated from the distance from the water surface to the interface with the targeted sludge and the settling speed of the sludge, and is preferably set, for example, within a range from 4 min/m to 15 min/m, and is more preferably set within a range from 5 min/m to 10 min/m. Further, the wastewater introduction rate (proportion of introduced water relative to the effective volume during reaction) is, for example, preferably at least 20% but not more than 120%, and is more preferably at least 40% but not more than 120%. It is thought that granulation of the sludge can be accelerated by allowing the sludge to repeatedly experience a state of extremely high concentration of the organic matter that represents the treatment target substance (immediately following the introduction step, a satiated state) and a state of extremely low concentration of the organic matter (at completion of the biological treatment step, a starved state), and therefore from the viewpoint of forming the granular sludge, the wastewater introduction rate is preferably as high as possible, but on the other hand, the higher the wastewater introduction rate becomes, the larger the pump capacity that is required, and the higher the costs become. Accordingly, from the viewpoints of ensuring favorable formation of the granular sludge and reducing costs, the wastewater introduction rate is preferably at least 40% but mot more than 120%. When the wastewater introduction rate is large, it is possible that the concentration of the wastewater discharged from the semibatch biological treatment tank may be poor, but because the discharged water is introduced into the continuous biological treatment tank, there is little chance of a deterioration in the concentration of the final treated water.

EXAMPLE

The present invention is described below in further detail using a series of examples and comparative examples, but the present invention is in no way limited by the following examples.

Example 1 and Comparative Example 1

A water flow test was performed using a semibatch reactor having a reactor effective volume of 3.5 L (length 70 mm×width 140 mm×height 360 mm). The SVI5 value was used as an indicator for evaluating the granulation. The SVI5 value is an indicator of the settling properties of the biological sludge, and is determined using the following method. First, 1 L of sludge is placed in a 1 L measuring cylinder, and following gentle stirring of the sludge to obtain as uniform a sludge concentration as possible, the sludge is left to stand for 5 minutes, and the sludge interface is then measured. The volume fraction (%) occupied by the sludge in the measuring cylinder is calculated. Next, the sludge MLSS value (mg/L) is measured. These values are then inserted into the following formula to calculate the SVI5 value. The smaller the SVI5 value, the better the sludge settling properties. An SVI5 value of 100 mL/g or less was deemed to indicate granules having good settling properties.

SVI5 (mL/g)=volume fraction occupied by sludge× 10,000/MLSS

The simulated wastewater that was used contained a fish meat extract and peptone as the main components, and was prepared with a BOD concentration of 80 to 120 mg/L.

The value (A value) obtained by multiplying the ratio of the MLSS concentration relative to the BOD load introduced into the semibatch reactor, by [total cycle time/reaction time], is determined in the following manner.

$A=((B-C)/1000\times(H\times D/100\times G))/(I/1000\times H))\times(F/E)$ wherein
B=wastewater BOD concentration [mg/L]
C=BOD concentration following treatment [mg/L]
D=wastewater introduction ratio relative to reactor effective volume per cycle [%]
E=biological treatment step time per cycle [minutes]
F=total process time per cycle [minutes]
G=number of cycles per day [cycles/day]
H=reactor effective volume [m$^3$]
I=MLSS [mg/L]

The operating cycle for the semibatch reactor was performed as follows.
(1) Introduction step: 1.75 L of the wastewater was introduced into the semibatch reactor.
(2) Biological treatment step: The ratio of the MLSS concentration relative to the BOD load (the A value in the above formula) was set to achieve the value shown in Table 1. In the biological treatment step, air was supplied from an aerator installed in the lower portion of the reactor, and a biological reaction was conducted.
(3) Settling step: the supply of air from the aerator was stopped, and the system was left to stand for 10 minutes to allow the sludge inside the reactor to settle.
(4) Discharge step: 1.75 L of the supernatant water was discharged as treated water.

The above steps (1) to (4) were repeated.

TABLE 1

| | Period [days] | A value [kgBOD/ kgMLSS/d] | Biological reaction step time per cycle [min] | SRT [days] | MLSS [mg/L] |
| --- | --- | --- | --- | --- | --- |
| Seed sludge | — | — | — | — | 5000 |
| Conditions 1 | 0 to 70 | 0.12 to 0.18 | 80 to 120 | No withdrawal | 3500 to 5500 |
| Conditions 2 | 71 to 90 | 0.12 | 100 to 120 | 30 | 4000 to 4700 |
| Conditions 3 | 91 to 104 | 0.25 | 85 | 30 | 3500 to 4000 |
| Conditions 4 | 105 to 140 | 0.1 | 85 to 120 | 25 | 4000 to 6500 |
| Conditions 5 | 141 to 200 | 0.1 to 0.16 | 100 to 150 | 15 | 3500 to 6500 |
| Conditions 6 | 200 to 220 | 0.22 | 100 | 15 | 3500 to 4000 |

The change over time in the SVI5 value under each set of conditions (conditions 1 to 3 in Table 1 (Comparative Example 1), and conditions 4 to 6 (Example 1)).

During the conditions 1 period, when water flow was started with the A value set to 0.12 to 0.18 kg/kg/d, the SVI5 value during the initial flow was about 60 mL/g, and SVI5 for 40 days of flow was from 50 to 60 mL/g, indicating good maintenance of the settling properties, but the SVI5 value tended to deteriorate after that point, and had worsened to 100 mL/g by the 75th day. During this period, no particular sludge withdrawal was performed, with the only sludge that was withdrawn being the SS incorporated in the treated water, meaning operations were performed with a sludge retention time (SRT) of about 30 to 100 days.

In the conditions 2 period, the A value was set to 0.12 kg/kg/d, and sludge withdrawal was started to set the SRT to 30 days, but the settling properties deteriorated even further than the state during the conditions 1, and SVI5 increased to about 110 mL/g.

In the conditions 3 period, the SRT was maintained at 30 days, and the reaction time was shortened, with the A value being increased from 0.12 kg/kg/d to 0.25 kg/kg/d, but the SVI5 value deteriorated even further, and had increased to 180 mL/g by the 104th day.

Figure 17:
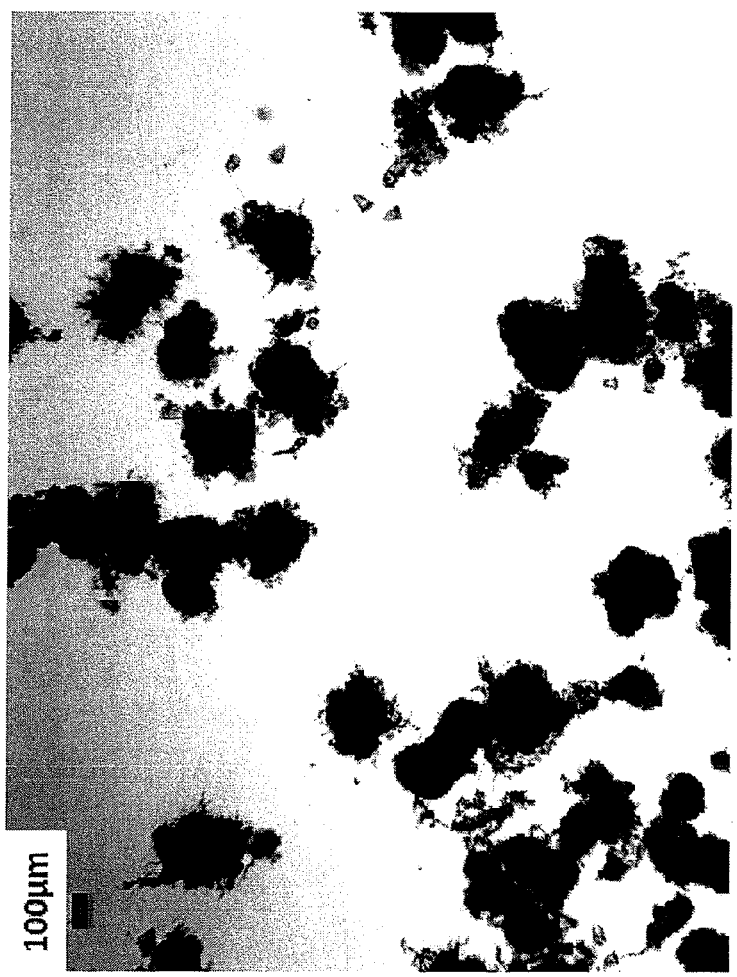
FIG. 17 is an electron microscope of a sludge in a period under conditions 2 and conditions 3 in Comparative Example 1.

Microscope observations of the sludge during the periods of conditions 2 and 3 revealed that although sludge having particles with a particle size of 200 μm or greater was observed, large amounts of flock sludge existed around these particles, and large numbers of protozoa and metazoa were also observed. It is thought that the fact that these protozoa and metazoa were feeding on the bacteria that should have been forming the targeted granules was one reason for the disintegration of the granules and the deterioration in the settling properties (see FIG. 17).

In the conditions 4 period, when the reaction time was lengthened, the A value was reduced to 0.1 kg/kg/d, and the sludge withdrawal was adjusted to achieve a SRT of 25 days, the SVI5 value started to decrease, and by the 140th day, had reduced to 90 mL/g and stabilized.

In the conditions 5 period, when the sludge withdrawal amount was adjusted to alter the SRT to 15 days, the SVI5 value started to decrease even further, and fell to 40 mL/g. The A value during this period was 0.1 to 0.16.

Figure 18:
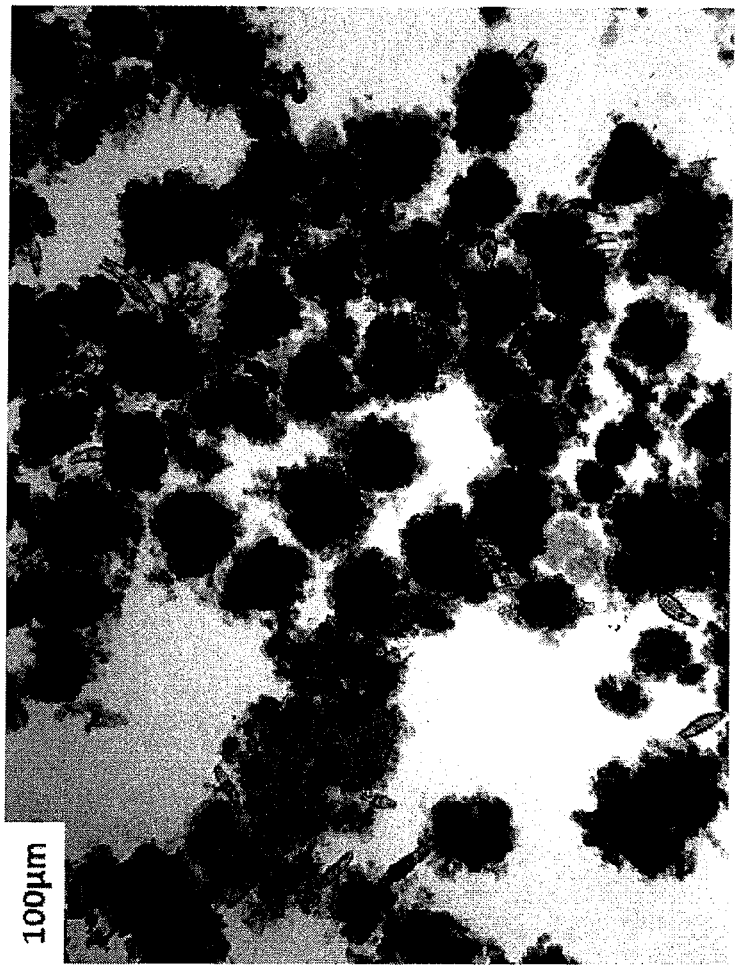
FIG. 18 is an electron microscope of a sludge in a period under conditions 5 and conditions 6 in Example 1.

In the conditions 6 period, the amount of sludge withdrawal was set to maintain the SRT at 15 days, and the reaction time was shortened to increase the A value to 0.22, but the SVI5 value stabilized at about 50 mL/g. In the conditions 3 period, the SVI5 deteriorated when the A value was increased to 0.25 with the SRT set to 30 days, but under the conditions 6 when the SRT was set to 15 days, it is thought that provided the A value was about 0.22, the granules could be maintained in a stable manner. Microscope observation during the period under the conditions 5 and 6 revealed that the abundance of flock sludge was reduced compared with the period under conditions 2 and 3, and large numbers of favorable granules having a particle size of about 200 to 300 μm were confirmed (see FIG. 18). Further, a reduction in the abundance of protozoa and metazoa was also confirmed.

Comparative Example 2

A water flow test was performed using a semibatch reactor having a reactor effective volume of 12 L (length 200 mm×width 150 mm×height 400 mm). In this test, a biologically treated water outlet was provided at the location of the water surface in the settling step, and at the same time that the wastewater was introduced, an electromagnetic valve on the biologically treated water outlet was opened, and the biologically treated water was discharged (see FIG. 5). The operating cycle was performed as follows.

(1) Introduction/discharge step: 9 L of the wastewater was introduced, and the biologically treated water was discharged.

(2) Biological treatment step: The ratio of the MLSS concentration relative to the BOD load (the A value in the above formula) was set to achieve a value of 0.03 to 0.04 kg/kg/d (see Table 2). In the biological treatment step, air was supplied from an aerator installed in the lower portion of the reactor, and a biological reaction was conducted.

(3) Settling step: the supply of air from the aerator was stopped, and the system was left to stand for 10 minutes to allow the sludge inside the reactor to settle. Further, sludge withdrawal was performed so as to achieve a SRT of 25 days.

TABLE 2

| | Period [days] | A value [kgBOD/ kgMLSS/d] | Biological reaction step time per cycle [min] | SRT [days] | MLSS [mg/L] |
|---|---|---|---|---|---|
| Seed sludge | — | — | — | — | 6000 |
| Conditions 7 | 0 to 50 | 0.03 to 0.04 | 250 to 300 | 20 | 4000 to 6000 |

Figure 15:
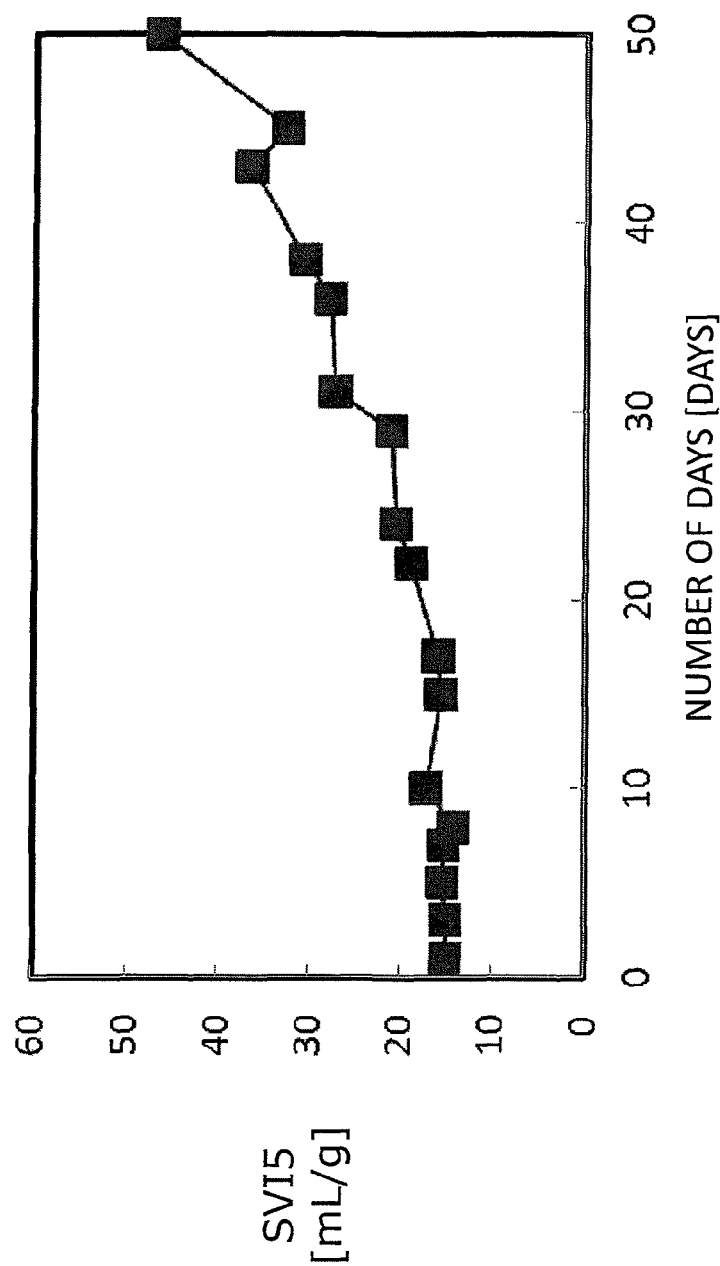
FIG. 15 is a diagram illustrating the change over time in SVI5 in Comparative Example 2.

The results are shown in FIG. 15. Operation was performed with an A value of 0.03 to 0.04, and a SRT of 25 to 30 days. The SVI5 during initial flow was about 15 mL/g, indicating extremely favorable settling properties, but the SVI5 tended to increase as flow was continued, and had worsened to 47 mL/g by the 50th day.

Example 2

A water flow test was performed using a semibatch reactor having a reactor effective volume of 12 L (length 200 mm×width 150 mm×height 400 mm). In this test, a biologically treated water outlet was provided at the location of the water surface in the settling step, and at the same time that the wastewater was introduced, an electromagnetic valve on the biologically treated water outlet was opened, and the biologically treated water was discharged (see FIG. 5). The operating cycle was performed as follows.

(1) Introduction/discharge step: 9.6 L of the wastewater was introduced, and the biologically treated water was discharged.

(2) Biological treatment step: The ratio of the MLSS concentration relative to the BOD load (the A value in the above formula) was set to achieve a value shown in Table 3. In the biological treatment step, air was supplied from an aerator installed in the lower portion of the reactor, and a biological reaction was conducted.

(3) Settling step: the supply of air from the aerator was stopped, and the system was left to stand for 10 minutes to allow the sludge inside the reactor to settle.

TABLE 3

|  | Period [days] | A value [kgBOD/ kgMLSS/d] | Biological reaction step time per cycle [min] | SRT [days] | MLSS [mg/L] |
|---|---|---|---|---|---|
| Seed sludge | — | — | — | — | 3000 |
| Conditions 8 | 0 to 40 | 0.15 to 0.2 | 170 to 200 | 7 to 10 | 2000 to 3000 |

Figure 16:
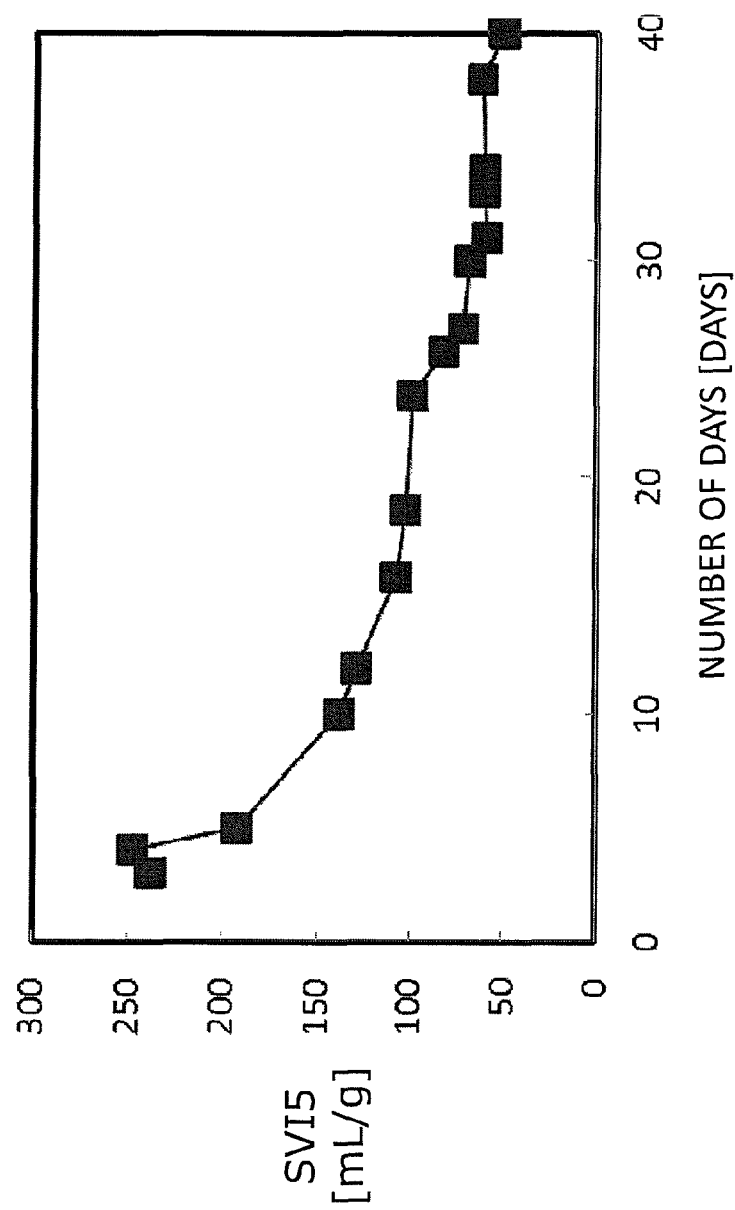
FIG. 16 is a diagram illustrating the change over time in SVI5 in Example 2.

The results are shown in FIG. 16. Operation was performed with an A value of 0.15 to 0.2, and a SRT of 7 to 10 days. The SVI5 during initial flow was about 250 mL/g, but the SVI5 tended to decrease as flow was continued, and had decreased to 51 mL/g by the 40th day, indicating that granules were able to be formed.

In this manner, by adjusting the reaction time so that the value obtained by multiplying the ratio of the MLSS concentration relative to the BOD load introduced into the semibatch reactor by [total cycle time/reaction time] was within a range from 0.05 to 0.25 kgBOD/kgMLSS/d, and performing sludge withdrawal such that the sludge retention time was 5 to 25 days, aerobic granules were able to be formed in a stable manner even in those cases where the wastewater BOD concentration was a low value of about 80 to 120 mg/L.

Example 3

Using a wastewater treatment device illustrated in FIG. 9, composed of a continuous biological treatment tank (114 L), a semibatch reactor (11 L) and a solid-liquid separation tank, a biological treatment test of a simulated wastewater was performed. The simulated wastewater that was used contained a fish meat extract and peptone as the main components, and was prepared with a BOD concentration of 80 to 120 mg/L and a total nitrogen concentration of 15 to 25 mgN/L.

In the continuous biological treatment tank, a 13.6 L anoxic tank, a 13.6 L aeration tank, a 19 L anoxic tank, a 19 L anoxic tank, a 24.5 L anoxic tank and a 24.5 L aeration tank were arranged in series, and a step-feed multistage nitrification-denitrification process (three stages) was used to treat the organic matter and the nitrogen components in the wastewater by injecting a third of the wastewater into each of the anoxic tanks. In the anoxic tanks, stirring was performed with a stirring device but without conducting aeration, whereas in the aeration tanks, aeration with air was performed using an air diffuser to generate a dissolved oxygen concentration of 1 to 5 mg/L. In the solid-liquid separator, settling separation was used to separate the sludge mixed liquid into a concentrated sludge and a treated water, and the concentrated sludge was returned to the first-stage anoxic tank. For the granule formation tank, the semibatch biological treatment tank illustrated in FIG. 3 was used. The treated water and granules from the granule formation tank were introduced into the first-stage anoxic tank of the continuous biological treatment tank.

Adjustment of the BOD load in the continuous biological treatment tank was performed by altering the amount of wastewater introduced. Further, adjustment of the retention time including the recirculation was performed by altering the wastewater flow rate calculated from the load, and the recirculation flow rate from the solid-liquid separator.

An activated sludge collected from a sewage treatment plant was used as the seed sludge introduced into the continuous biological treatment tank. The seed sludge was a sludge of typical settling properties, having an SVI value of 200 mL/g, and an average particle size for the activated sludge of about 80 μm.

Prior to passing the water through the continuous biological treatment tank, the semibatch biological treatment tank was used to form a granular sludge using the aforementioned simulated wastewater. The thus formed granular sludge was a granular sludge having an average particle size of 340 μm, in which the volume fraction of particles of at least 200 μm was 85%.

Table 4 summarizes the various conditions used during the water flow test (MLSS in the continuous biological treatment tank, BOD sludge load and BOD volume load in the continuous biological treatment tank, and actual retention time (retention time including the recirculation flow rate from the solid-liquid separator)), and the sludge SVI value 50 days after changing to each of the conditions.

TABLE 4

|  | Period days | MLSS mg/L | BOD sludge load kgBOD/kgMLVSS/d | BOD volume load kgBOD/m³/d | Actual retention time h | SVI mL/g |
|---|---|---|---|---|---|---|
| Seed sludge | — | 1500 | — | — | — | 200 |
| Conditions 1 | 0 to 50 | 1500 | 0.08 | 0.1 | 10 to 14 | 150 |
| Conditions 2 | 50 to 100 | 1500 | 0.05 to 0.07 | 0.08 | 10 to 12 | 300 |
| Conditions 3 | 100 to 150 | 1500 | 0.12 to 0.18 | 0.15 to 0.28 | 8 to 10 | 60 |
| Conditions 4 | 150 to 200 | 1500 | 0.12 to 0.18 | 0.15 to 0.2 | 10 to 12 | 120 |
| Conditions 5 | 200 to 250 | 1500 to 4500 | 0.08 to 0.1 | 0.15 to 0.4 | 5 to 8 | 65 |
| Conditions 6 | 250 to 300 | 4500 | 0.08 to 0.1 | 0.4 | 5 to 8 | 90 |

Under the conditions 1 which included an MLSS of 1500 mg/L and a BOD sludge load of 0.08 kgBOD/kgMLVSS/d, supply of the granular sludge from the semibatch biological treatment tank and flow of the simulated wastewater were started. The SVI gradually decreased from the start of water flow, and had decreased to about 150 mug by the 50th day. During this period, the retention time including the recirculation was 10 to 14 hours. It is thought that because the activated sludge of the seed sludge was not acclimatized to the simulated wastewater, no significant improvement was observed.

Next, the load was lowered by reducing the amount of wastewater introduced, and a water flow test was performed under the conditions 2, with the BOD sludge load set to a value of 0.05 to 0.07 kgBOD/kgMLVSS/d. The actual retention time was 10 to 12 hours. In the water flow test under the conditions 2, the SVI of the sludge in the continuous biological treatment tank increased as the test proceeded, and reached a value of about 300 mL/g. When the sludge inside the continuous biological treatment tank was observed under a microscope, the existence of granules in the sludge could not be confirmed. It is thought that this indicates disintegration of the granules.

Subsequently, the amount of wastewater introduced was increased, and a water flow test was performed under the conditions 3, with the BOD sludge load set to a value of 0.12 to 0.18 kgBOD/kgMLVSS/d. The actual retention time was 8 to 10 hours. In the water flow test under the conditions 3, the SVI of the sludge inside the continuous biological treatment tank decreased rapidly, decreasing to 100 mL/g after 15 days, and then down to a final value of 60 mL/g. Based on these results, it can be stated that disintegration of the granular sludge had been suppressed, and a granular sludge having favorable settling properties had been maintained inside the biological treatment tank.

Next, with the BOD sludge load maintained, a water flow test was performed under the conditions 4, in which the retention time was altered to 10 to 12 hours by lowering the recirculation flow rate. In the water flow test under the conditions 4, the SVI value of the sludge inside the continuous biological treatment tank exhibited an increasing trend, but stabilized at about 120 mL/g, indicating that a granular sludge having comparatively favorable settling properties had been maintained.

Subsequently, when a water flow test was performed under the conditions 5, with the BOD sludge load set to about 0.08 to 0.1 kgBOD/kgMLVSS/d and the retention time set to about 5 to 8 hours, the SVI developed a declining trend, and decreased to 65 mL/g. During this period, an increase in the sludge concentration and an increase in the load were trialed as the settling properties improved, and the MLSS was increased to 4,500 mg/L and the BOD volume load was increased to 0.4 kgBOD/m$^3$/d.

Next, when a water flow test was performed under the conditions 6, with the MLSS set to 4,500 mg/L and the BOD volume load set to 0.4 kgBOD/m$^3$/d, stable operation was able to be achieved with the SVI maintained at 90 mL/g.

Figure 19:
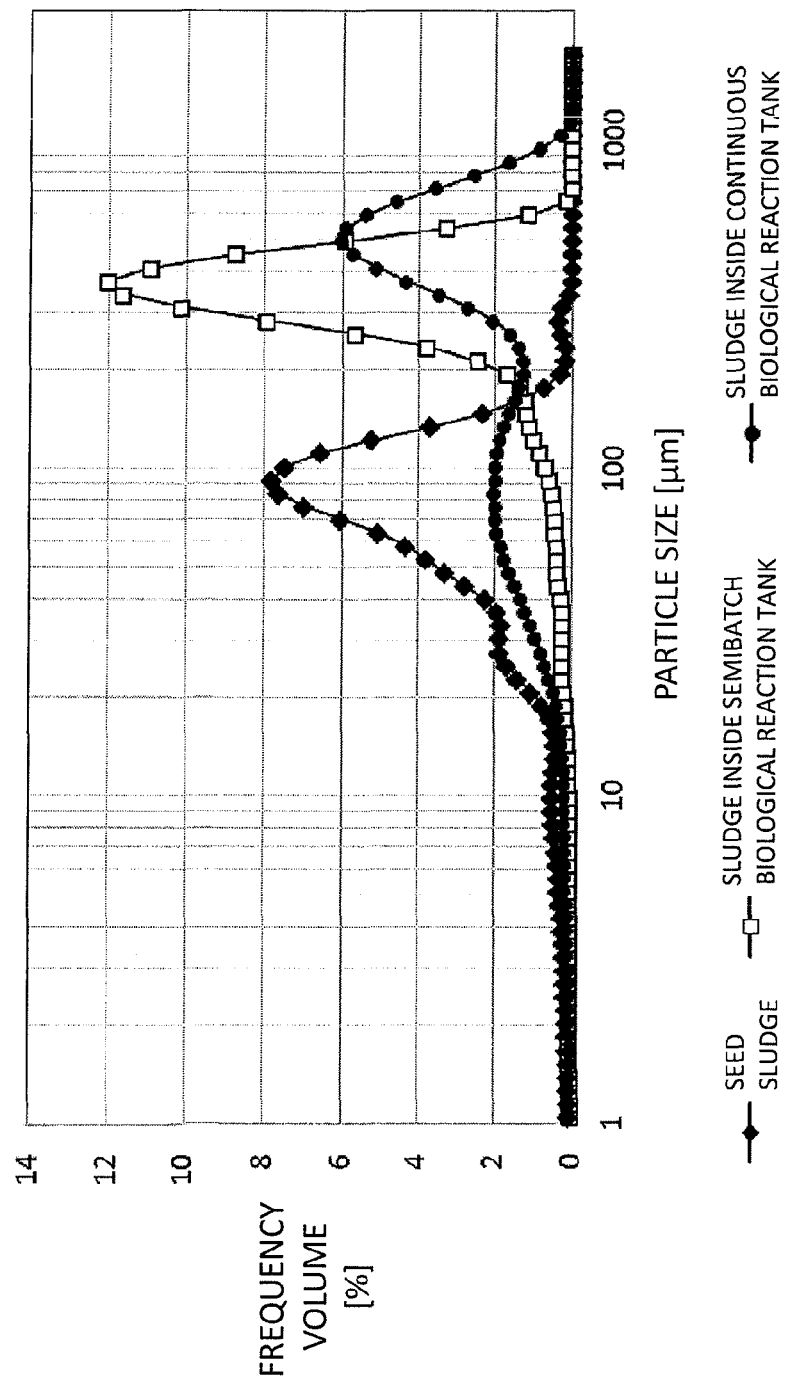
FIG. 19 is a diagram illustrating the particle size distributions of a seed sludge, a granular sludge formed in a semibatch biological treatment tank, and a sludge inside a continuous biological treatment tank under conditions 6.

FIG. 19 is a diagram illustrating the particle size distributions of the seed sludge, the granular sludge formed in the semibatch biological treatment tank, and the sludge inside the continuous biological treatment tank under the conditions 6. The seed sludge had an average particle size of about 80 μm, and the granular sludge formed in the semibatch biological treatment tank was a sludge containing particles with a particle size of 300 μm or greater. Further, in the sludge inside the continuous biological treatment tank under the conditions 6, although some sludge having a particle size of about 80 μm existed, a sludge having a particle size of about 300 to 500 μm was also confirmed. In other words, it is thought that the particle size of the granular sludge is increasing inside the continuous biological treatment tank.

During the flow periods under the conditions 1 to 6, the water quality of the final treated water included a BOD value of not more than 5 mg/L, and a TN concentration of not more than 10 mg/L.

Comparative Example 3

A water flow test was performed under conditions in which granular sludge was not supplied from the semibatch biological treatment tank to the continuous biological treatment tank. In the same manner as the examples, an activated sludge collected from a sewage treatment plant was used as the seed sludge. The properties of the seed sludge included an SVI value of 180 mL/g. Table 5 summarizes the various conditions used during the water flow test (MLSS in the continuous biological treatment tank, BOD sludge load and BOD volume load in the continuous biological treatment tank, and actual retention time (retention time including the recirculation flow rate from the solid-liquid separator)), and the sludge SVI value 20 days after changing to each of the conditions.

TABLE 5

|  | Period days | MLSS mg/L | BOD sludge load kgBOD/kgMLVSS/d | BOD volume load kgBOD/m$^3$/d | Actual retention time h | SVI mL/g |
| --- | --- | --- | --- | --- | --- | --- |
| Seed sludge | — | 1500 | — | — | — | 180 |
| Conditions 7 | 0 to 20 | 1500 | 0.06 to 0.08 | 0.08 to 0.1 | 10 to 14 | 250 |
| Conditions 8 | 20 to 40 | 1500 | 0.12 to 0.16 | 0.14 to 0.18 | 10 to 12 | 200 |
| Conditions 9 | 40 to 60 | 1500 | 0.08 to 0.1 | 0.1 to 0.12 | 8 to 10 | 200 |

First, a water flow test was performed under the conditions 7, with the BOD sludge load set to 0.06 to 0.08 kgBOD/kgMLVSS/d. The results revealed a gradual deterioration in the settling properties of the seed sludge, with the SVI value increasing to 250 mL/g.

Next, when a flow test was performed under the conditions 8, with the BOD sludge load set to 0.12 to 0.16 kgBOD/kgMLVSS/d, although the settling properties exhibited a slight improving trend, the SVI stagnated at 200 mL/g.

Subsequently, a water flow test was performed under the conditions 9, with the BOD sludge load set to 0.08 to 0.1 kgBOD/kgMLVSS/d, but there was no change in the settling properties, and the SVI value remained at 200 mL/g.

The settling properties were unable to be significantly improved in any of the periods under the various conditions 7 to 9. As a result, the treatment rate could not be increased by increasing the MLSS concentration.

Based on the results of Example 3 and Comparative Example 3, it can be stated that in a system in which a granular sludge having a particle size of 200 μm or greater is supplied to a continuous biological treatment tank, by operating the system so that the BOD sludge load falls within a range from 0.08 to 0.2 kgBOD/kgMLVSS/d, the MLSS can be set to 4,000 mg/L or higher, while suppressing disintegration of the granular sludge and maintaining favorable settling properties, meaning a high treatment rate can be obtained.

REFERENCE SIGNS LIST

1: Granule formation device
3 to 9: Wastewater treatment device
10: Semibatch reactor
12: Wastewater inlet pump
12a: Wastewater inlet
12d: Treated water outlet
14: Aeration pump
15: Recirculation line
16: Biologically treated water outlet
18: Biologically treated water discharge valve
20: Control device
22: Sludge withdrawal port 24: Sludge withdrawal pump
26: Aerator
28: Wastewater supply line
30: Biologically treated water line
32: Sludge withdrawal line
34: Motor
36: Stirring blade
38: Wastewater inlet valve
40: Wastewater inlet
42: Wastewater discharge unit
49: Stirring device
50: Wastewater storage tank
52, 52a, 52b, 52c: Continuous biological treatment tank
52d: Anoxic tank
52e: Aeration tank
52f: Anaerobic tank
54: Solid-liquid separator
56, 59, 60, 64: Pump
58, 62, 63: Valve
61: Sludge and treated water supply line
66, 66a: Wastewater supply line
68: Sludge line
70: Line
72: Treated water line
74: Sludge discharge line
76: Sludge return line

The invention claimed is:

1. A method for forming aerobic granules using a semibatch reactor, the method comprising forming granules by repeatedly performing an introduction introducing an organic matter-containing wastewater containing organic matter, a biological treatment biologically treating treatment target substances in the organic matter-containing wastewater using a microbial sludge, a settling allowing the microbial sludge to settle, and a discharge discharging a biologically treated water that has been biologically treated, wherein
   a reaction time is adjusted so that a value obtained by multiplying a ratio of an MLSS concentration relative to a BOD load introduced into the semibatch reactor by [total cycle time/reaction time] falls within a range from 0.05 to 0.25 kgBOD/kgMLSS/d, and the sludge is withdrawn such that a sludge retention time is 5 to 25 days.

2. The method for forming aerobic granules according to claim 1 wherein,
   a biologically treated water outlet of the semibatch reactor is provided above a wastewater inlet, and the biologically treated water is discharged from the biologically treated water outlet by introducing the organic matter-containing wastewater into the semibatch reactor.

3. A method for treating a wastewater, the method comprising supplying granules formed by the method for forming aerobic granules according to claim 1 to a continuous biological treatment tank used for biologically treating an organic matter-containing wastewater with a biological sludge, while the organic matter-containing wastewater is introduced continuously.

4. The method for treating a wastewater according to claim 3, wherein
   the granules are a granular sludge having a particle size of 200 μm or greater, and
   a BOD sludge load of the continuous biological treatment tank is within a range from 0.08 to 0.2 kgBOD/kgMLVSS/d.

5. The method for treating a wastewater according to claim 3, wherein
   the continuous biological treatment tank comprises multiple reaction tanks.

6. The method for treating a wastewater according to claim 3, wherein
   the method comprises a sludge return separating a biological sludge by a solid-liquid separation from a biological treatment liquid that has undergone treatment in the continuous biological treatment tank, and then returning the separated biological sludge to the continuous biological treatment tank, and
   a hydraulic retention time for the continuous biological treatment tank, determined from a sum of a flow rate of wastewater introduced into the continuous biological treatment tank and a flow rate of the biological sludge returned to the continuous biological treatment tank, and a volume of the continuous biological treatment tank, is within a range from 5 hours to 10 hours.

7. The method for treating a wastewater according to claim 3, wherein
   in the introduction in the method for forming aerobic granules, a portion of the wastewater supplied to the continuous biological treatment tank is introduced into the semibatch reactor.

8. A device for forming aerobic granules comprising a semibatch reactor that forms granules by repeatedly performing an introduction introducing an organic matter-containing wastewater containing organic matter, a biological treatment biologically treating treatment target substances in the organic matter-containing wastewater using a microbial sludge, a settling allowing the microbial sludge to settle, and a discharge discharging a biologically treated water that has been biologically treated and
   a control device that controls a reaction time of the biological treatment in the semibatch reactor and sludge withdrawal, wherein
   the control device is programmed to adjust the reaction time of the biological treatment so that a value obtained by multiplying a ratio of an MLSS concentration relative to a BOD load introduced into the semibatch reactor by [total cycle time/reaction time] falls within a range from 0.05 to 0.25 kgBOD/kgMLSS/d, and the sludge is withdrawn such that a sludge retention time is 5 to 25 days.

9. The device for forming aerobic granules according to claim 8, wherein
   the device has a biologically treated water outlet of the semibatch reactor provided above a wastewater inlet, and the biologically treated water is discharged from the biologically treated water outlet by introducing the organic matter-containing wastewater into the semibatch reactor.

10. A device for treating a wastewater comprising:
    a continuous biological treatment tank used for biologically treating an organic matter-containing wastewater with a biological sludge, while the organic matter-containing wastewater is introduced continuously;
    the device for forming aerobic granules according to claim 3; and
    a supply device supplying granules formed by the device forming aerobic granules according to claim 3 to the continuous biological treatment tank.

11. The device for treating a wastewater according to claim 10, wherein
- the granules are a granular sludge having a particle size of 200 μm or greater, and
- a BOD sludge load of the continuous biological treatment tank is within a range from 0.08 to 0.2 kgBOD/kgMLVSS/d.

* * * * *